US010842357B2

(12) United States Patent
Moskowitz et al.

(10) Patent No.: US 10,842,357 B2
(45) Date of Patent: Nov. 24, 2020

(54) ENDOSCOPIC SURGICAL SYSTEM

(71) Applicant: Moskowitz Family LLC, Rockville, MD (US)

(72) Inventors: Mosheh T. Moskowitz, Rockville, MD (US); Nathan C. Moskowitz, Rockville, MD (US); Randal B. Chinnock, Ashford, CT (US); Jason P. Julian, Rutland, MA (US); George Grubner, Needham, MA (US); Ahmnon D. Moskowitz, Rockville, MD (US)

(73) Assignee: Moskowitz Family LLC, Rockville, MD (US)

( * ) Notice: Subject to any disclaimer, the term of this patent is extended or adjusted under 35 U.S.C. 154(b) by 851 days.

(21) Appl. No.: 14/049,743

(22) Filed: Oct. 9, 2013

(65) Prior Publication Data

US 2014/0213848 A1    Jul. 31, 2014

Related U.S. Application Data

(60) Provisional application No. 61/712,251, filed on Oct. 10, 2012.

(51) Int. Cl.
*A61B 1/00* (2006.01)
*A61B 17/00* (2006.01)
(Continued)

(52) U.S. Cl.
CPC .......... *A61B 1/00133* (2013.01); *A61B 1/018* (2013.01); *A61B 17/00234* (2013.01);
(Continued)

(58) Field of Classification Search
CPC .............. A61B 17/00234; A61B 17/29; A61B 17/2909; A61B 17/320016;
(Continued)

(56) References Cited

U.S. PATENT DOCUMENTS 5,478,351 A     12/1995  Meade et al.
5,879,289 A *   3/1999   Yarush ............... A61B 1/00039
                                                      600/109

(Continued)

FOREIGN PATENT DOCUMENTS

DE           10156917 A1 *  6/2003   ......... A61B 17/2909

OTHER PUBLICATIONS

Bissinger, G (DE 10156917A1); English Translation through Espacenet. (Year: 2003).*

*Primary Examiner* — Ryan N Henderson
*Assistant Examiner* — Pamela F Wu
(74) *Attorney, Agent, or Firm* — Fish & Richardson P.C.

(57) ABSTRACT

The present invention is an apparatus, device or tool for performing endoscopic (that is, minimally invasive) surgery. An exemplary embodiment of the invention includes a video endoscope whilst in another embodiment of the invention includes an endoscopic surgical tool which, when equipped with one of a suite of endoscopic surgical instruments, can be used by a surgeon to perform surgical procedures inside a body. Another embodiment of the present invention includes a suite of endoscopic surgical instruments designed to work co-operatively with the endoscopic surgical tool. In another embodiment of the present invention, a video-assisted endoscopic surgical tool system is provided. In one embodiment, the system includes the video-assisted endoscopic surgical tool and a suite of at least one endoscopic surgical instrument.

17 Claims, 16 Drawing Sheets

(51) Int. Cl.
*A61B 1/018* (2006.01)
*A61B 17/29* (2006.01)
*A61B 90/00* (2016.01)

(52) U.S. Cl.
CPC .............. *A61B 17/29* (2013.01); *A61B 90/37* (2016.02); *A61B 2017/0046* (2013.01); *A61B 2017/00464* (2013.01); *A61B 2017/00477* (2013.01); *A61B 2017/292* (2013.01); *A61B 2090/372* (2016.02); *A61B 2217/007* (2013.01)

(58) Field of Classification Search
CPC ............ A61B 17/3201; A61B 17/3421; A61B 1/00052; A61B 1/00135; A61B 1/018; A61B 2017/0046; A61B 2017/00469; A61B 2017/2929; A61B 1/001131; A61B 1/00133; A61B 1/00105; A61B 1/00064; A61B 1/00066; A61B 1/012; A61B 1/0125; A61B 2017/00464; A61B 2017/00367; A61B 2017/00477; A61B 2017/291; A61B 2017/2912–2919; A61B 2017/292; A61B 2017/2922–2929; A61B 2017/293; A61B 2017/2931–2934; A61B 2017/2936–2937; A61B 2017/2939; A61B 2017/294; A61B 2017/2941; A61B 2017/2943–2944
USPC ........ 600/104–106, 109–110, 128, 130–131, 600/137, 153, 160; 606/205
See application file for complete search history.

(56) References Cited

U.S. PATENT DOCUMENTS

| | | | | |
|---|---|---|---|---|
| 5,928,137 A | * | 7/1999 | Green | A61B 1/00052 600/104 |
| 5,928,255 A | * | 7/1999 | Meade | A61B 17/29 600/564 |
| 6,221,007 B1 | * | 4/2001 | Green | A61B 1/00052 600/104 |
| 6,261,307 B1 | * | 7/2001 | Yoon | A61B 17/29 600/101 |
| 2002/0082475 A1 | * | 6/2002 | Stahl | A61B 1/00147 600/114 |
| 2004/0133075 A1 | * | 7/2004 | Motoki | A61B 1/00039 600/131 |
| 2004/0204628 A1 | * | 10/2004 | Rovegno | A61B 1/00052 600/131 |
| 2006/0167340 A1 | * | 7/2006 | Pease | A61B 1/00052 600/127 |
| 2008/0076966 A1 | * | 3/2008 | Isaacson | A61B 1/303 600/106 |
| 2008/0154299 A1 | * | 6/2008 | Livneh | A61B 17/2909 606/205 |
| 2008/0314958 A1 | * | 12/2008 | Scirica | A61B 17/07207 227/175.2 |
| 2010/0016885 A1 | * | 1/2010 | Eidenschink | A61B 1/018 606/213 |
| 2010/0094090 A1 | * | 4/2010 | Mejia | A61B 1/00052 600/120 |
| 2011/0065992 A1 | * | 3/2011 | Bissinger | A61B 17/2909 600/131 |

* cited by examiner

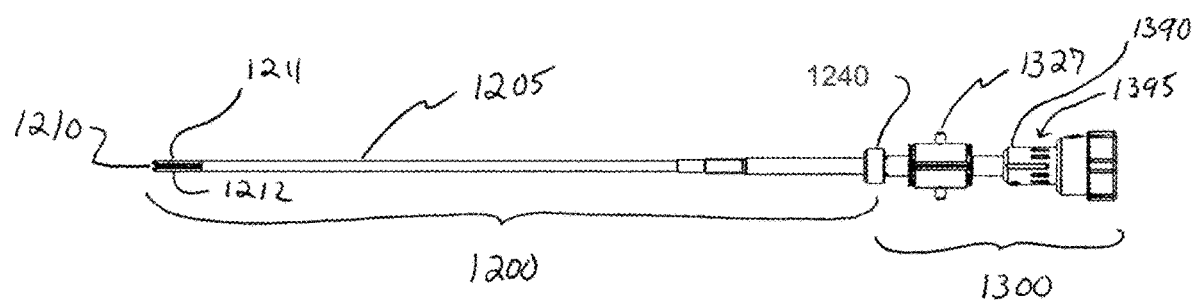
FIG. 7A
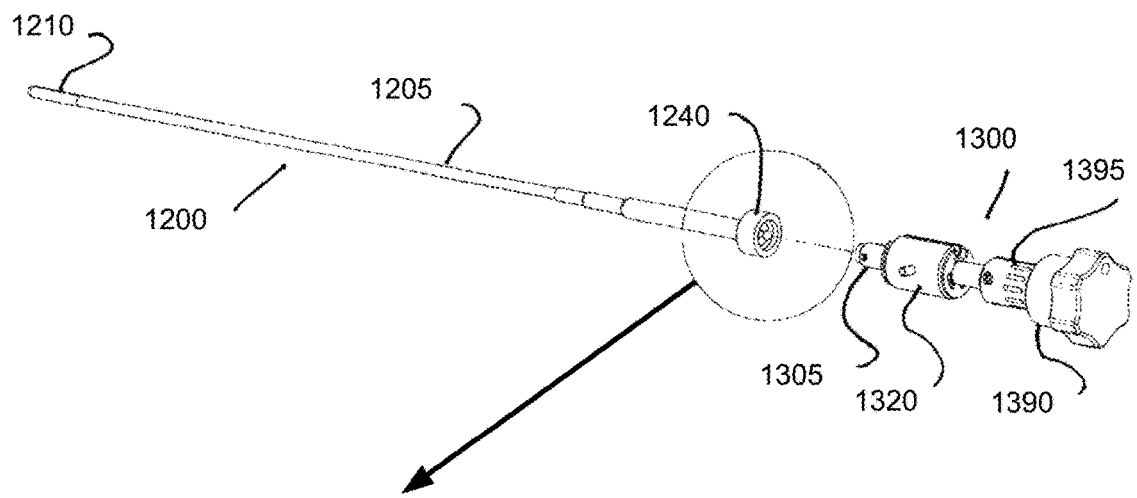
FIG. 7B
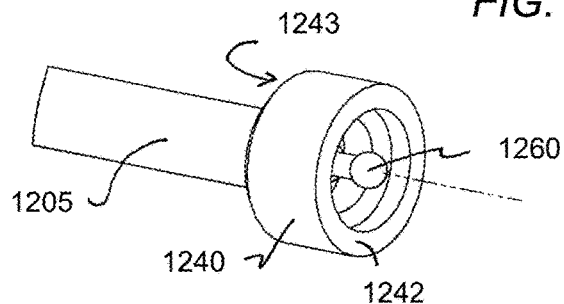
FIG. 7B1

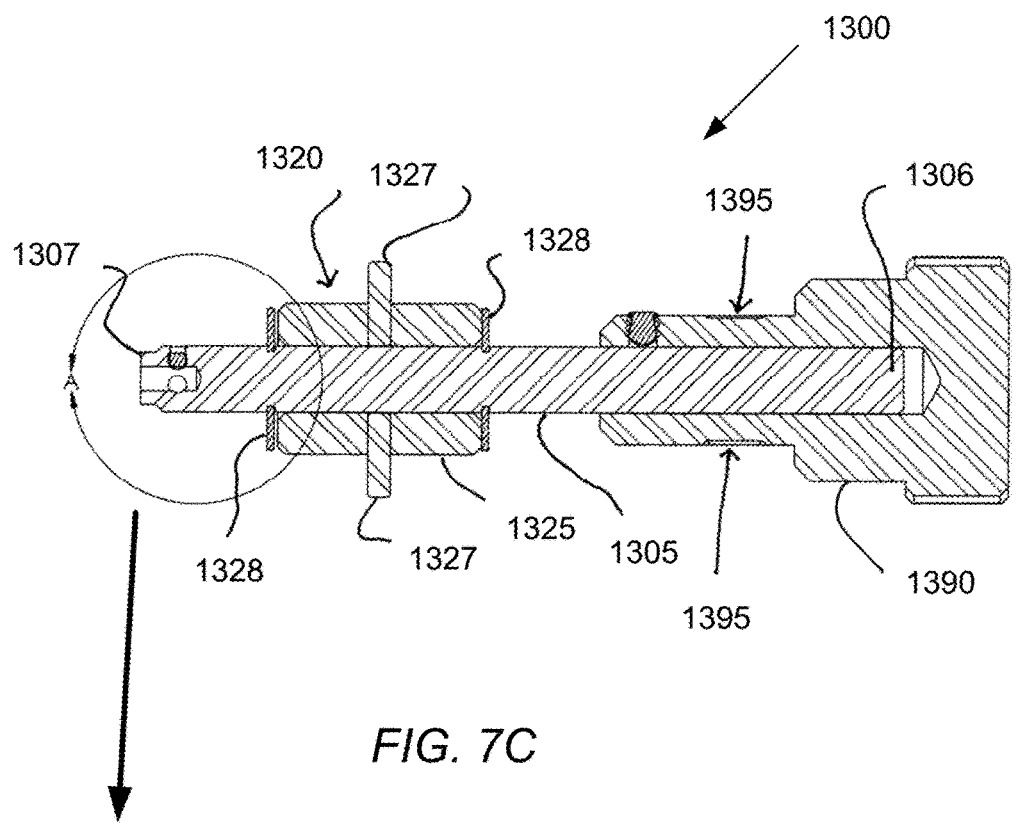
FIG. 7C
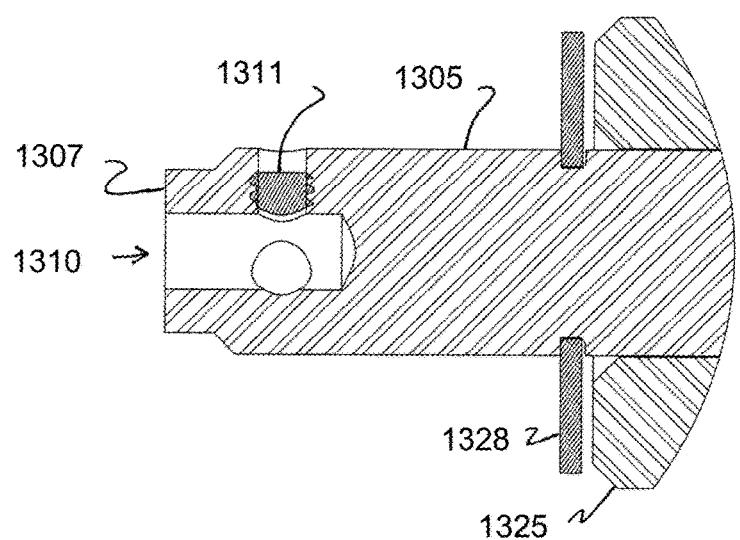
FIG. 7C1

ENDOSCOPIC SURGICAL SYSTEM

CROSS-REFERENCE TO RELATED APPLICATIONS

This application claims the benefit under Title 35, U.S.C. § 119 (e) of U.S. provisional application 61/712,251, filed on Oct. 10, 2012, the entire contents of which are hereby incorporated by reference and for which priority is claimed under 35 U.S.C. § 120.

FIELD OF THE INVENTION

The present invention generally relates to the field of endoscopic surgery, and more particularly, to the field of video-assisted endoscopic surgery, and more particularly, to the field of video-assisted endoscopic surgical instruments.

BACKGROUND OF THE INVENTION

Endoscopic surgery, sometimes known as minimally invasive surgery, which also includes percutaneous endoluminal and transluminal procedures, comprises the creation by the surgeon of one or more access openings in a patient's body skin, cavity, skull, sinus, through which one or more thin, surgical devices are inserted. At least one of these devices is a visualization device (an endoscope) that allows the surgeon to see what is happening inside the patient. The additional devices are the actual surgical instruments the surgeon manipulates, and can include the insertion of implants to perform and/or augment the desired procedure.

In some endoscopic surgeries the endoscope and the surgical instruments are individual, independent devices, and they are usually inserted through separate access openings. Generally the endoscope is left in place (although it may be re-aimed) throughout the surgery while the surgical instruments are inserted and removed as needed to accomplish the specific surgical tasks for which they were designed.

More recently, endoscopic surgical tools have been developed in which the endoscopic function and the surgical function are combined into a single device. This combined function device is advantageous in two ways; first, only a single device needs to be inserted into the patient and manipulated by the surgeon and second, the visualization system in the endoscope is pre-aligned in the direction of the effector end of the surgical instrument.

One drawback to a combined endoscope/surgical instrument device is that visualization is lost if and when the surgeon needs to withdraw the surgical instrument in favor of a different instrument; when the instrument is withdrawn from the patient, the visualization system is withdrawn simultaneously.

This drawback can be overcome with a combined endoscopic surgical device in which the instrument is replaceable during a procedure—that is, a combined device from which the surgical instrument can be removed and replaced. Meade et al, in U.S. Pat. No. 5,478,351, teaches a method of removing and replacing an endoscopic surgical instrument from its mating control handle. However the approach taught therein is not suitable for the combined endoscopic surgical tool; the instrument in Meade's device is removed and replaced from a port on the distal end of the control handle. For a combined endoscopic surgical device, the replaceable instrument must be removed from the proximal end of the control handle assembly, leaving the video sensor inside the patient.

One system that combines an endoscope with proximally replaceable surgical instruments is taught by Green in U.S. Pat. No. 5,928,137. Essentially Green teaches a surgical tool adapted to accept custom design, proximally replaceable instruments, wherein a single insertion tube for the surgical instrument has a second, separate channel or bore into which is inserted a complete and integral video endoscope, several commercially available endoscopes being suggested as suitable for use. The control of the video endoscope is inherently separate from the control handles for the surgical instrument. By design, the surgical instruments cannot rotate relative to the control handles although the bore of the video endoscope can be rotated about the insertion tube axis to provide a view from "above" or "below" the instrument end effector.

There exists, therefore, a need for a truly integrated-by-design endoscopic surgical tool in which the electronic and opto-mechanical elements of the endoscope and the elements of the surgical instrument controls are compactly combined.

Additionally, there is a need for an endoscopic surgical tool with proximally replaceable instruments in which the instrument orientation about its longitudinal axis can be set independently of the tool's permanent control handle.

Further, the need exists for a surgical tool with proximally replaceable instruments wherein existing commercially available instruments can be easily modified to be proximally loaded.

There also is a need for an endoscopic surgical tool that can proximally accept without modification existing commercially available surgical instruments.

A further need remains for an endoscopic surgical tool wherein both the video electronics control and the surgical instrument can be operated with one hand by the surgeon.

BRIEF SUMMARY OF THE INVENTION

The present invention is direct to an apparatus, device or tool for performing endoscopic (that is, minimally invasive) surgery. An exemplary embodiment of the invention comprises a video endoscope, permitting the surgeon to view a conveniently located electronic video image of the surgical site inside the body whilst in another exemplary embodiment of the invention comprises a endoscopic surgical tool which, when equipped with one of a suite of endoscopic surgical instruments, can be used by a surgeon to perform surgical procedures inside a body.

In one exemplary embodiment, the tool comprises an extended, multi-channeled, tubular body and a multi-functional handle assembly wherein the tubular body may be inserted through a small incision into a patient's body while the handle assembly remains exterior to the body.

In another exemplary embodiment, the tool further comprises a video imaging subsystem, typically comprising a video image sensor and compatible support optics and electronics whereby a video image signal stream of the region immediately in front of, or oblique to the front of, the tool is produced. In yet another exemplary embodiment, the tool comprises an illumination subsystem, the subsystem comprising light sources and light transfer and projection optical elements, whereby illumination for the video imaging subsystem is projected on the region immediately in front of or oblique to the front of the tool.

In some exemplary embodiments, the tool further comprises a video display unit. The video display unit, in some embodiments, is mechanically attached to and in electronic communication with the tool while in other embodiments the video display unit is only in electronic communication with the tool and is disposed at a remote location. In some embodiments, this electronic communication is wireless.

In another exemplary embodiment, the tool is designed to function co-operatively with a removable endoscopic surgical instrument, wherein the surgical instrument is operationally disposed within a channel in the tubular body, extending axially from the proximal end of the body to the distal end of the body. In some embodiments, the handle assembly comprises an axial captivation mechanism for holding the removable instrument in a fixed, operating position along the axis of the body. In other embodiments, the handle assembly comprises an angular captivation mechanism for holding the removable instrument in one or more angular positions. In some embodiments, the handle assembly further comprises at least one articulated control lever. The control lever may be movable to an instrument exchange position, wherein a removable instrument may be removed from or inserted into the device, and also movable through a range of surgical instrument operational positions, wherein the surgical instrument operates in accordance with its design. Other embodiments of the handle assembly may comprise more than one articulated control lever.

Another exemplary embodiment of the present invention is directed to a suite of endoscopic surgical instruments designed to work co-operatively with the endoscopic surgical tool.

In one exemplary embodiment, each instrument in the suite of endoscopic surgical instruments comprises an extended, hollow sheathing body and a distal end, surgical effector. Generally, a surgical instrument comprises a driving connector, disposed within the lumen of the sheathing body and extending the length thereof, to transmit forces and/or motions from the proximal end of the sheathing body to the distal end surgical effector. In another exemplary embodiment, each instrument comprises one or more proximal end interface adaptors, the interface adaptors designed to operate co-operatively with the axial and/or angular captivation mechanisms and control lever(s) in the handle assembly. In one exemplary embodiment, the interface adaptor(s) transmit and/or convert the movements of and forces generated by the control lever(s) from the lever(s) to the sheathing body and/or the driving connector therein.

In another exemplary embodiment, the device is configured to accept the insertion of third party supplied endoscopic surgical instruments, wherein the third-party instruments have no special adaptations to work co-operatively with the endoscopic surgical tool.

In another exemplary embodiment, the present invention is a video-assisted endoscopic surgical tool system. In one aspect the system comprises the video-assisted endoscopic surgical tool and a suite of at least one endoscopic surgical instrument, wherein the suite of surgical instruments has been designed to work co-operatively with the endoscopic surgical tool.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

The foregoing and other objects, features and advantages of the invention will become apparent from the following description in conjunction with the accompanying drawings, in which reference characters refer to the same parts throughout the different views. The drawings are not necessarily to scale; emphasis has instead been placed upon illustrating the principles of the invention. Of the drawings:

FIG. 7A is top view of a surgical instrument designed to work with the surgical tool, according to an exemplary embodiment;

FIG. 7B is a partial exploded view of a surgical instrument designed to work with the surgical tool, according to an exemplary embodiment;

FIG. 7B1 is a detail view of the proximal end of a surgical instrument's instrument effector subassembly according to an exemplary embodiment;

FIG. 7C is a sectional view of a handle engagement interface adaptor according to an exemplary embodiment;

FIG. 7C1 is a detail view of the distal end of the handle engagement interface adaptor of FIG. 7C according to an exemplary embodiment.

DETAILED DESCRIPTION OF THE EXEMPLARY EMBODIMENTS OF THE INVENTION

Figure 1:
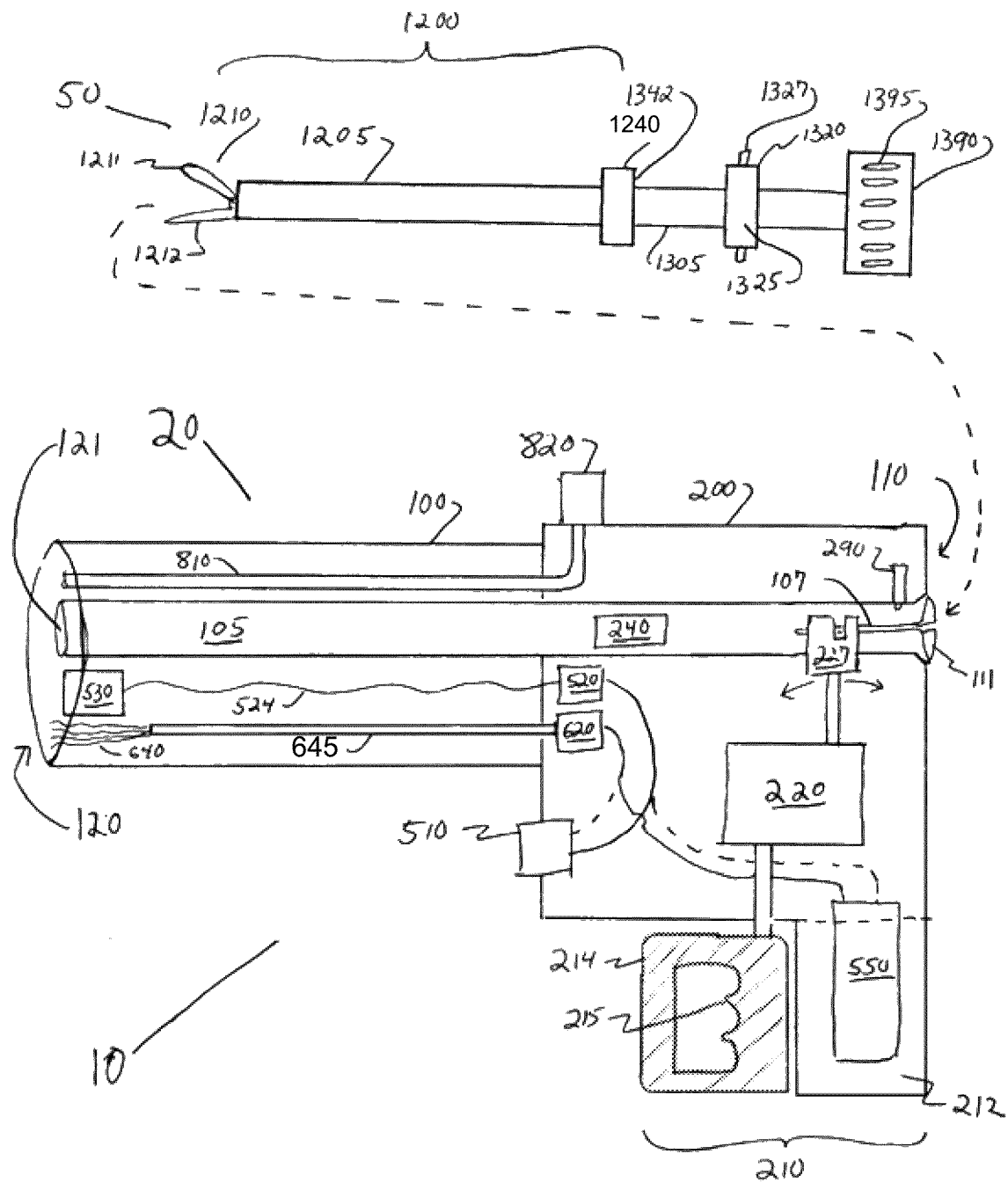
FIG. 1 is functional block diagram of a surgical system according to an exemplary embodiment.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Referring now to the drawings, FIGS. 1-8 illustrate exemplary embodiments of an endoscopic surgical system 10.

FIG. 1 is a functional block diagram illustrating the major elements of an endoscopic surgical system 10. System 10 primarily comprises an endoscopic surgical tool 20 and at least one surgical instrument 50. Surgical tool 20 comprises a generally tubular body assembly 100 and a control handle assembly 200. Body assembly 100 comprises a proximal end 110 and a distal end 120 and generally penetrates handle assembly 200, handle assembly 200 being substantially disposed at proximal end 110. Surgical instrument 50 is designed to be replaceably inserted into body assembly 100 through an insertion port 111 at proximal end 110, as will be discussed below. In use, a surgeon inserts or has an assistant insert an instrument 50 into body assembly 100, holds system 10 by a handle grip 210 and inserts distal end 120 into a patient through a pre-prepared surgical opening.

Tubular body assembly 100 comprises an instrument guide channel 105. Guide channel 105 comprises a hollow tube that effectively traverses at least the entire length of body assembly 100, starting at insertion port 111 at proximal end 110 and ending at an exit port 121 at distal end 120. As will be described below in the context of an exemplary embodiment, guide channel 105 typically may comprise multiple, concatenated segments of sequentially decreasing diameter. Additionally, particular segments may be designed to facilitate mechanical interactions between surgical tool 20 and surgical instrument 50. In particular, channel guide 105 comprises one or two open-ended drive-pin guide slots 107 disposed to run axially, starting with their open end at proximal end 110 and ending at a pre-determined distance towards distal end 120, where the guide slots' end points are a design choice. Typically the slots are disposed diametrically opposed in the X-Y plane as illustrated in the figure. In other embodiments the slot or slots may be disposed elsewhere around the circumference of channel guide 105.

Surgical tool 20 further comprises a video imaging subsystem 500, the disparate elements of the subsystem being disposed at least partly in body assembly 100. Imaging subsystem 500 comprises two major elements; a miniaturized video camera head 530 that contains an image sensor and various image forming optical elements disposed at distal end 120 and a video processor 520, disposed conveniently within system 10. Video processor 520 is designed to work co-operatively and conventionally with the electronics in camera head 530 to produce a standard format video stream.

Some elements of imaging subsystem 500 may be disposed in handle assembly 200 when it is convenient to the designer to do so. Power supplies (for example, batteries) and human interface control devices (jointly indicated by callout 550) are typically disposed in handle assembly 200. Alternatively power supplies and/or control devices may be located remotely from system 10, in which configuration a suitable electrical connector is provided.

In one embodiment, video imaging subsystem 500 comprises a display signal output interface 510. The output interface 510 is designed to provide the connection between tubular body assembly 100 or handle assembly 200 and an auxiliary video display device, not illustrated. Output interface 510 may be wired or wireless, may comprise a signal only interface or a signal plus power interface, and may be electronic, mechanical, or both. In some embodiments the auxiliary video display device may be comprise video processor 520. In one exemplary embodiment the auxiliary video display device is both mechanically attached to system 10 at output interface 510 and receives a video image signal from imaging subsystem 500 through output interface 510. In other embodiments output interface 510 may also be used to connect the system's electrical components to an external power source; that is, output interface 510 may be used as the above mentioned suitable electrical connector.

Surgical tool 20 further comprises an illumination subsystem 600, the disparate elements of the subsystem being disposed in body assembly 100 and handle assembly 200. The illumination subsystem comprises two major elements; a low power light source assembly 620, which contains, typically, a low-power white light source such as a "white" LED and miscellaneous coupling optics, if needed, and an incoherent bundle 645 of at least two multi-mode optical fibers 640. Fiber bundle 645 delivers light from the conveniently disposed source assembly 620 to distal end 120. Fiber bundle 645 may be encased in a protective jacket for at least part of the distance between source assembly 620 and distal end 120, or may be totally unjacketed. At distal end 120, fibers 640 in bundle 645 are spread out to fill the empty spaces around the other elements, for example, video head 530 and exit port 121, that are disposed at distal end 120. Electrical power and/or control devices for the light source may be provided by a battery, typically located in handle assembly 200, or they may be located remotely from system 10, in which configuration a suitable electrical connector is provided. Note that power supplies and control devices 550 may be shared between video imaging subsystem 500 and illumination subsystem 600.

In some embodiments, surgical tool 20 further comprises an irrigation channel 800. Irrigation channel 800 is conventional in design and typically comprises a fluid input/output (I/O) port 820 disposed very generally towards proximal end 110 and a fluid transport tube 810 running through the interior of body assembly 100 from I/O port 820 to an irrigation port 830 disposed at distal end 120.

In some embodiments, one or more human interface control devices 550 for imaging subsystem 500 are incorporated into handle grip 210. Disposition of control devices 550 (for example, switches to control on/off, brightness, contrast, etc.) as part of handle grip 210 allows the surgeon to adjust the imaging system performance to meet his needs without releasing grip 210 or releasing the instrument in his other hand or calling instructions to an assistant.

Returning to FIG. 1, handle assembly 200 comprises handle grip 210 with an articulated grip 214 and a reaction grip 212. Handle assembly 200 further comprises several captivating and/or force transfer mechanisms that interact with a surgical instrument disposed in guide channel 105. Of the latter mechanisms, an axial retainer 240 is disposed on or adjacent to guide channel 105. In one embodiment, axial retainer 240 comprises a moveable retaining bar (not illustrated in FIG. 1) that may be moved effectively transversely to the axis of guide channel 105 to lock a surgical instrument in place axially. In the locking position, at least a portion of the retaining bar protrudes into the lumen of channel guide 105; in the unlock position the retaining bar is withdrawn from the lumen of channel guide 105 at least far enough to allow a surgical instrument to move axially unimpeded through the channel guide.

During installation of co-operatively designed surgical instrument 50 into channel guide 105, the movable retaining bar is disposed in its "unlock" position; that is, it is withdrawn from the lumen of guide channel 105 to allow the instrument to be inserted without impediment. Once instrument 50 is disposed and fully seated in guide channel 105, the moveable retaining bar is moved into the lumen where it interacts with an axial retaining collar 1340 on the instrument. Typically, axial retaining collar 1340 has a flat bearing face 1342 disposed on its proximal side or, alternatively has a moderately deep, circumferential groove that is designed to accept the retaining bar. When the bar moved into the lumen of guide channel 105, instrument 50 is constrained from moving axially toward proximal end 110 because the bar bears against either flat bearing face 1342 or the distal wall of the groove. Instrument 50 is, however, free to rotate around its axis as there is no barrier on bearing face 1342 or in the groove to hit the bar and constrain rotation.

Handle assembly 200 also comprises a rotation captivation/indexing mechanism 290. Rotation captivation mechanism 290 is also disposed in close proximity to channel guide 105. Rotation captivation mechanism 290 comprises a movable element that protrudes into the lumen of channel guide 105 and that is designed to interact with a co-operatively designed collar on an installed instrument. In one embodiment rotation captivation is accomplished by a friction brake, wherein movable element may be a threaded rod with a friction pad affixed to one end, that end disposed to press against the co-operatively designed collar. Pad pressure, and therefore friction, is increased or decreased by an operator by tightening or loosening the thread. In another embodiment, the movable element is a spring or ball plunger and the co-operatively designed collar comprises a set of shallow, axially-aligned grooves disposed around the outer circumference of the collar. Each groove serves as a detent stop, or index location, as the instrument is rotated about its axis.

Handle assembly 200 further comprises the mechanism for controlling the operation of surgical instrument 50. The controlling mechanism comprises, firstly, handle grip 210, secondly a force transfer yoke 227, and thirdly, a set of connecting linkages 220, wherein the relative motion between articulated grip 214 and reaction grip 212 is transferred and converted by connecting linkages 220 to force transfer yoke 227. Force transfer yoke 227 is designed to engage and disengage with a mating element on a surgical instrument inserted into guide channel 105. Force transfer yoke 227 is further designed to move said mating element forward and backward along the axis of guide channel 105.

Force transfer yoke 227 comprises, in typical embodiments, a two pronged head piece that is disposed on a stalk 220A, stalk 220A also being a linkage in linkage set 220. In one embodiment the two prongs of yoke 227 are disposed at diametrically opposed locations across channel guide 105, generally towards proximal end 110. Each prong has an open ended drive-pin slot 229, the slots being oriented substantially perpendicular to the axis of channel guide 105 when stalk 220A is in its nominal position, that is, substantially parallel to the Z-axis of the figure. By design, drive-pin slots 229 are disposed to line up with drive-pin guide slots 107 in channel guide 105. In other embodiments yoke 227 will be designed to have drive-pin slot(s) 229 match the location of drive-pin guide slot(s) 107. In one embodiment, guide channel 105 may comprise a single drive-pin guide slot disposed along the bottom of guide channel 105 and transfer yoke 227 may comprise a single drive-pin slot at the top of stalk 220A. It will be noted that the yoke/drive pin design is but one mechanism for transferring force/motion between tool 20 and surgical instrument 50. Other mechanisms, such as magnetic interaction, may be used to connect a moving part in handle 200 to a surgical instrument without intruding into the lumen of guide channel 105.

Handle grip 210, as its name suggests, is the handle by with the surgeon holds and controls surgical tool system 10. Grip 210 comprises the articulated and the reaction grip, which move relative to each other when squeezed by the surgeon. Conventionally, reaction grip 212 is fixed relative to the rest of surgical tool 20 and is shaped to fix into the surgeon's palm whilst the surgeon's fingers are engaged by finger indentations 215 disposed on the distal side of articulated grip 214. When squeezed, articulated grip 214 moves proximally and drives mechanical linkage set 220 which in turn moves stalk 220A in a proximal direction.

Figure 2:
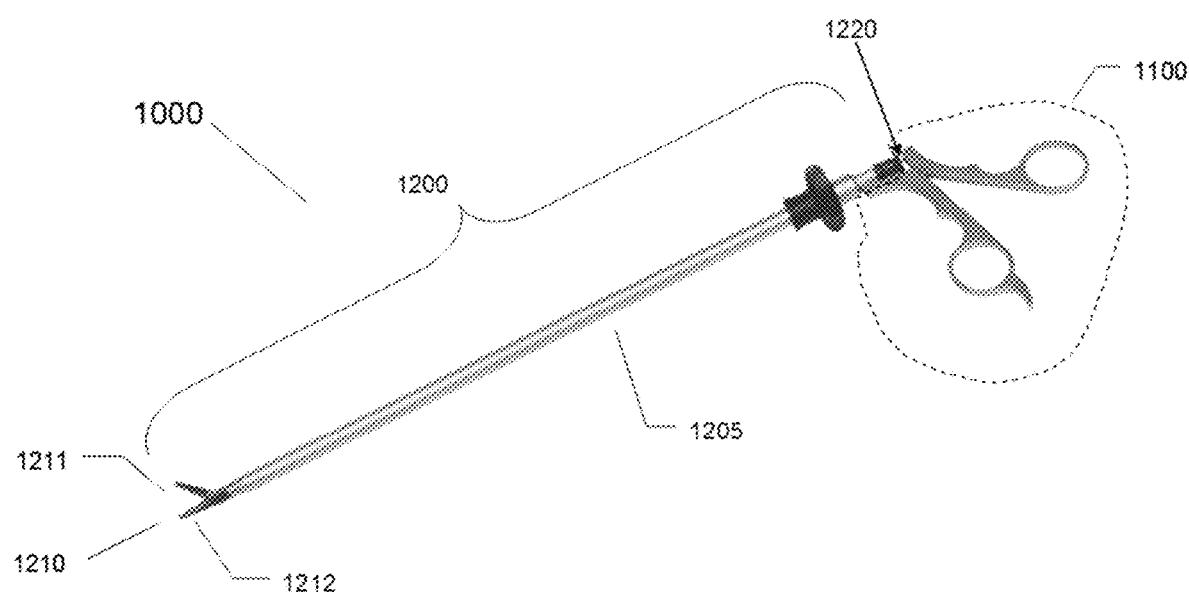
FIG. 2 illustrates a prior art endoscopic surgical instrument.

Surgical tool system 10 further comprises surgical instrument 50. As shown in FIG. 2, a conventional, prior art, minimally invasive surgical instrument 1000 comprises a manipulator subassembly 1100 and an instrument effector subassembly 1200. Effector subassembly 1200 comprises an extended sheathing body 1205, which is substantially a hollow tube, an end effector 1210, and a driving connector 1220. Driving connector 1220 is an extended wire or rod which runs the length of sheathing body 1205 and has a proximal end that is connected to manipulator subassembly 1100 and a distal end that is connected to end effector 1210. In FIG. 2, only the very proximal tip of the driving connector wire is visible in the gap between sheathing body 1205 and manipulator subassembly 1100. End effector 1210 is the "working" part of the surgical instrument and may comprise gripping jaws, a wire noose, scissors, or any other surgical device comprising at least two elements between which one degree of mechanical motion is needed. In this prior art example, end effector 1210 is a pair of gripping jaws: fixed jaw 1212 and articulated jaw 1211. Articulated jaw 1211 is disposed on a hinge mechanism and connected to the distal end of driving connector 1220. Articulated jaw 1211 is configured to have a normal (e.g., unactivated) disposition in the illustrated "open" position and to close against fixed jaw 1212 when driving connector is pulled proximally toward manipulator subassembly 1100. Typically, a spring or other source of restoring force is disposed inside sheathing body 1205. The restoring force is directed in opposition to any proximal motion of driving connector 1220 and acts to return articulated jaw 1211 to its normal, open disposition in the absence of any proximally directed force along driving connector 1220.

The prior art manipulator subassembly 1100 comprises two relatively articulated levers, in this example a fixed lever 1110 and a moving lever 1120. Fixed lever 1110 is effectively attached to sheathing body 1205 and moving lever 1120 is attached to the proximal end of driving connector 1220. Manipulator subassembly 1110 is configured such that squeezing moving lever 1120 towards fixed lever 1110 pulls driving connector 1220 in the proximal direction, which motion in turn is transferred to end effector 1210, causing articulated jaw 1211 to close against fixed jaw 1212.

Surgical instrument 50 is, substantially, a conventional minimally invasive surgical instrument that has been modified to operate in conjunction with surgical tool 20. As shown in FIG. 1, instrument 50 joins an instrument effector subassembly 1200 that is functionally equivalent to the prior art to a handle engagement interface adaptor 1300 designed in co-operation with surgical tool 20.

Instrument effector subassembly 1200, in addition to elements described in the prior art of FIG. 2, comprises axial retaining collar and a driving connector attachment interface, which is an interface element connected to the proximal end of driving connector 1220. Axial retaining collar and the driving connector attachment interface support three functional requirements in some preferred embodiments;

axial retention, rotational torque transfer, drive force/motion transfer. Axial retaining collar is rigidly attached to sheathing body 1205 to prevent any substantive axial or rotational relative displacement between the two. Once in place, as described above, axial retaining collar is prevented from moving toward proximal end 110 by the moveable retaining bar of axial retainer 240. Locking retaining collar in place perforce locks sheathing body 1205 in place as well. Axial retaining collar and the driving connector attachment interface are also used as the interface between instrument effector subassembly 1200 and a tool interface connector 1305. Tool interface connector 1305 moves axially to activate end effector 1210 and rotationally to rotate end effector 1210. Collar and attachment interface are designed in coordination with tool interface connector 1305 to transfer rotational torque from the latter to instrument effector subassembly 1200 and to transfer axial motion or force from the latter to driving connector 1220 only.

Handle engagement interface adaptor 1300 comprises tool interface connector 1305, an axial force transfer collar 1320, and a rotation index collar 1390. Tool interface connector 1305, as described above, is essentially a rod of rigid material that is the intermediary means of transferring motions or forces from the surgeon to end effector 1210. Tool interface connector 1305 is equipped with a connector, not illustrated, designed in co-ordination with axial retaining collar, to transfer axial motion/forces to driving connector 1220 and rotational motion/forces to instrument effector subassembly 1200.

Handle engagement interface adaptor 1300 comprises axial force transfer collar 1320, which transfers axial motion/force from force transfer yoke 227 to tool interface connector 1305. In one embodiment, axial force transfer collar 1320 comprises a toroidal ring 1325 from which one or more drive pins 1327 project radially. Drive pins 1327 have a diameter and projection length designed to allow them to extend through drive-pin guide slots 107 and further through drive-pin slots 229. Ring 1325 is disposed to encircle tool interface connector 1305 and is further disposed axially along tool interface connector 1305 at a location proximal from bearing face 1242 that corresponds to the distance in handle assembly between axial retainer 240 and force transfer yoke 227. The interior diameter of the hole in ring 1325 is slightly larger than the exterior diameter of tool interface connector 1305 to allow ring 1325 to smoothly rotate about connector 1305. Ring 1325 is captivated axially by retainers on both its proximal and distal sides. Thus, ring 1325 can spin in place axially on tool interface connector 1305.

Handle engagement interface adaptor 1300 also comprises rotation index collar 1390. Rotation index collar 1390 may be a ring or an end cap on tool interface connector 1305. Index collar 1390 is typically rigidly attached to interface connector 1305 in both the axial and rotational degrees-of-freedom but must be attached to at least prevent a rotational motion about tool interface connector 1305. Index collar 1390 is designed to work co-operatively with rotation captivation mechanism 290 to position and hold surgical instrument 50 at one or more desired angular rotation positions relative to handle assembly 200. In one preferred embodiment, rotation captivation mechanism 290 comprises a spring or ball plunger. In that embodiment, index collar 1390 comprises a set of one or more shallow, axially-aligned, detent grooves 1395 disposed around the outer circumference of index collar 1390. Grooves are used instead of mere spherical indentations to accommodate the axial motion of interface connector 1305 when the surgical instrument is being operated.

EXEMPLARY EMBODIMENT

Figure 3A:
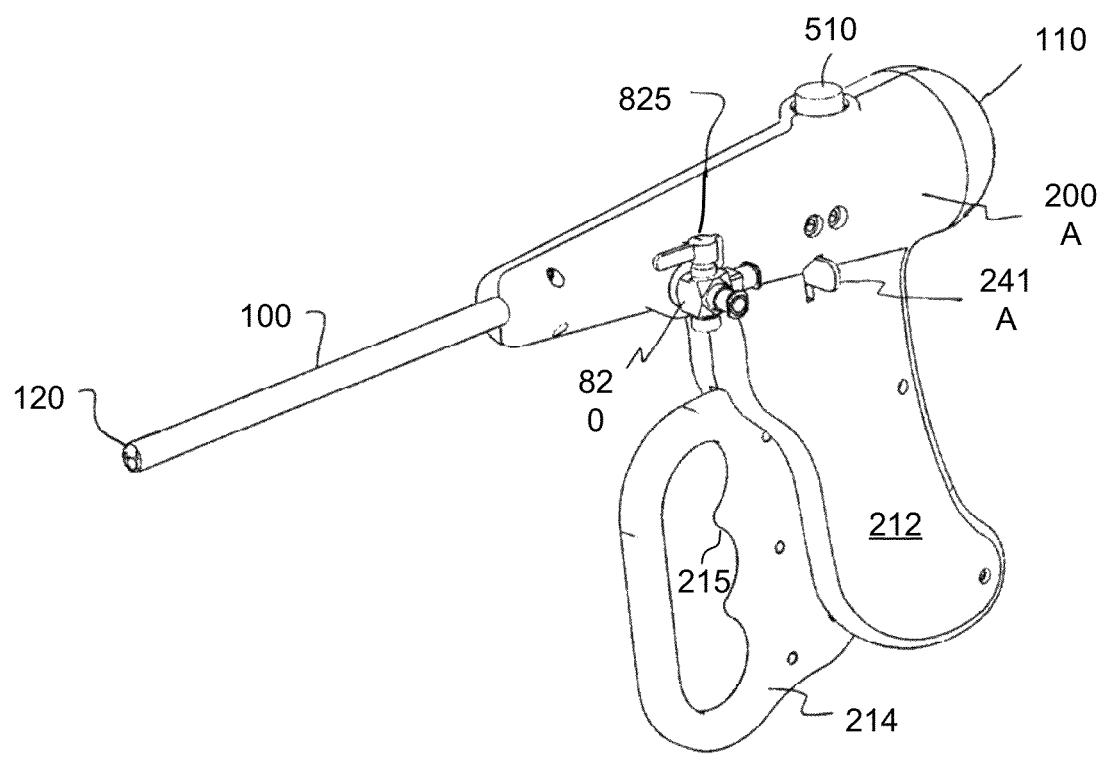
FIG. 3A is an isometric illustration of a surgical tool, as viewed generally from its distal end, according to an exemplary embodiment.
Figure 3B:
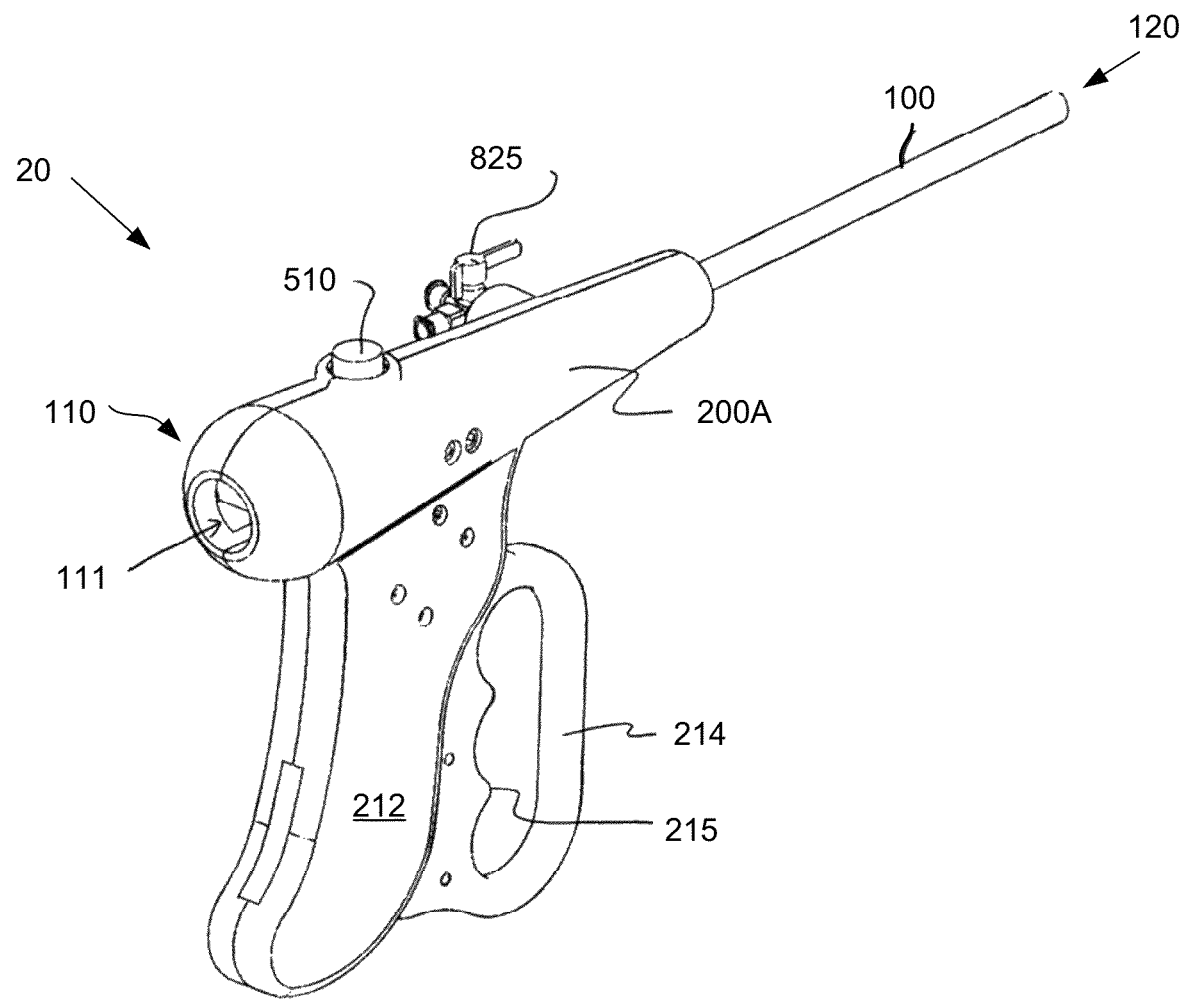
FIG. 3B is an isometric illustration a surgical tool, as viewed generally from its proximal end, according to an exemplary embodiment.
Figure 4A:
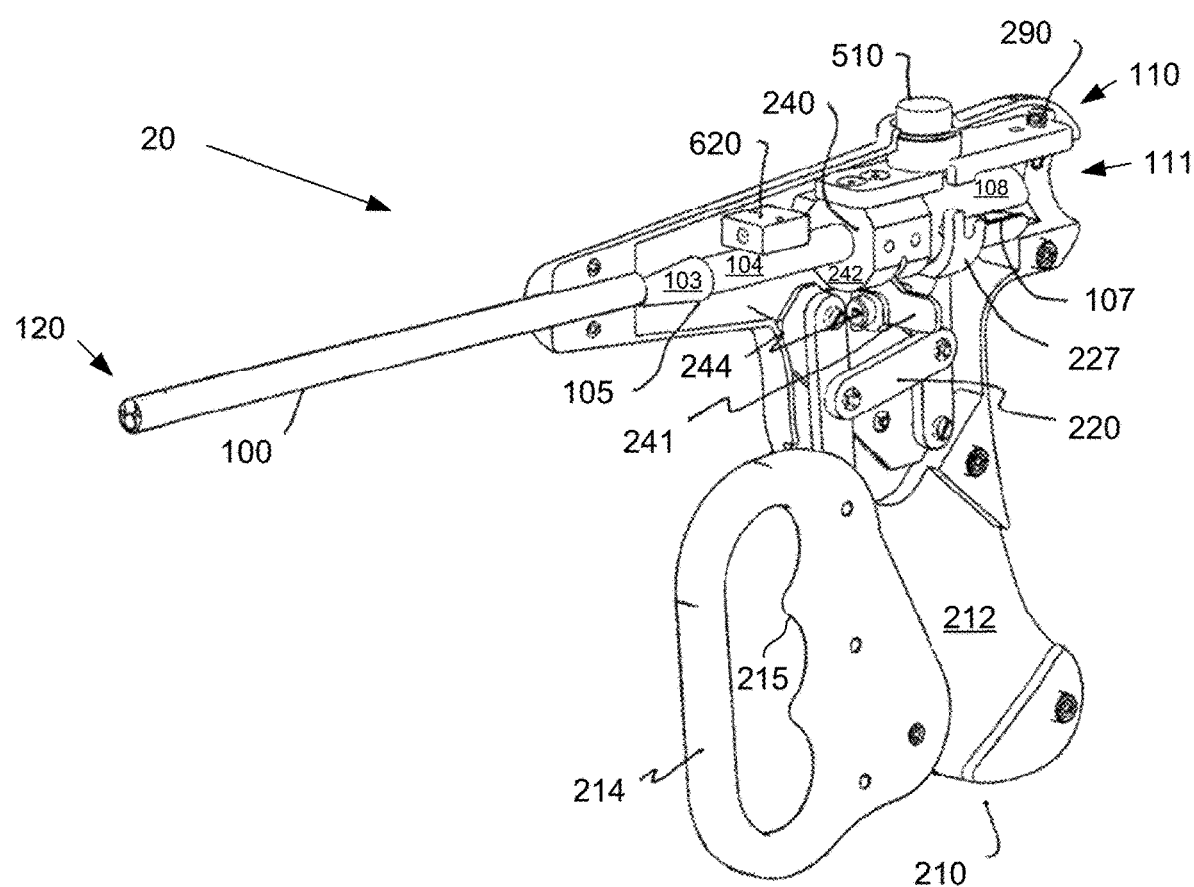
FIG. 4A is an isometric illustration of a surgical tool with side panel removed, as viewed generally from its distal end, according to an exemplary embodiment.
Figure 4B:
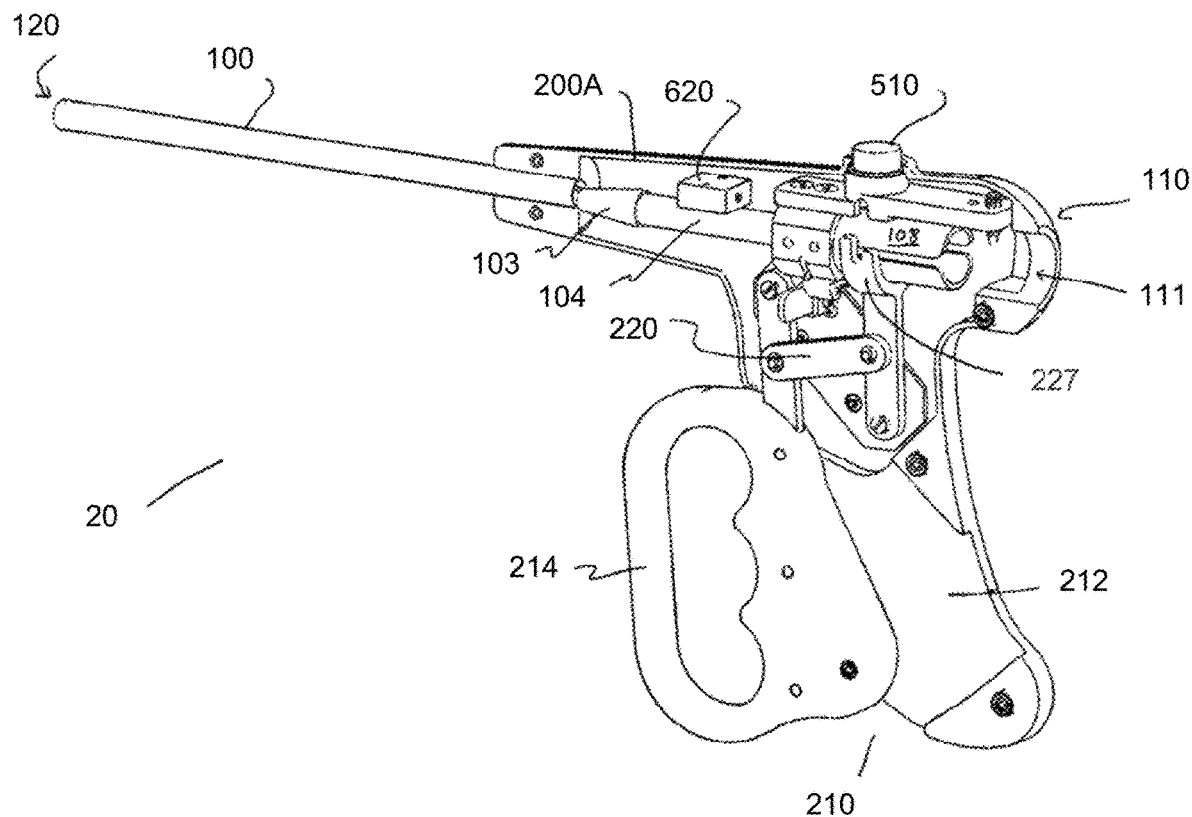
FIG. 4B is an isometric illustration of a surgical tool with side panel removed, as viewed generally from its proximal end, according to an exemplary embodiment.

FIG. 3A is an isometric illustration of an exemplary embodiment of surgical tool 20 as viewed generally from its distal end 120. FIG. 3B illustrates the same embodiment viewed generally from proximal end 110. FIG. 4A is an isometric view similar to FIG. 3A of this same embodiment but with a side panel removed to show the interior components. FIG. 4B is the same panel-removed embodiment as FIG. 4A except it has been rotated to show a view from the distal end. In general and unless otherwise specified, surgical tool 20 is fabricated from materials commonly used in surgical instruments suitable for sterilization, for example, by autoclave. Typically, stainless steel is used.

With reference to these four Figures, in this embodiment, tubular body assembly 100 comprises a thin walled, hollow, typically metal tube extending from a distal end 120 to the distal tip of control handle assembly 200, where the length of the tube is a design choice to meet a surgeon's need to operate inside a patient's body. Typically the length of tubular body 100 is between 10 centimeters and 30 centimeters with a circular cross-sectional shape and a diameter of between 0.2 centimeters and 1.5 centimeters. Tubes of different lengths, cross-sectional shapes, and/or effective cross-sectional diameters are considered to be within the scope of this invention.

In this exemplary embodiment, control handle assembly 200 has an exterior housing 200A that comprises a pistol style handle grip 210 where reaction grip 212 is fixed and integral to housing 200A whilst articulated grip 214 is D-shaped with a number of finger indentations 215.

On the near side (left side as viewed from proximal end 110) of handle assembly 200, fluid I/O ports 820, with a three position control valve 825 providing off, irrigate, or suction, is disposed above handle grip 210. While convenient for left handed valve operation (when surgical tool is held in the right hand) this valve and port may be disposed on the right side as a surgeon's preference item. I/O ports 820 and three position valve 825 are conventional in design and may be purchased commercially, for example, as Part #6001 from Cadence, Inc., 9 Technology Drive. Staunton, Va. 24401.

A tip 241A of an embodiment of a movable retaining bar 241 is also visible in FIG. 3A. Tip 241A protrudes from the left side of housing 200A. As may be best seen in FIGS. 4A and 4B, retaining bar 241 is part of axial retainer 240. In this embodiment, retaining bar 241 is a generally L-shaped flat plate with a pivot point disposed at the apex of the "L". Retaining bar 241 is inserted or withdrawn from the lumen of axial retainer 240 by pushing up or down on protruding tip 241A, which action pivots the other arm of the "L" into or out of the lumen.

Returning to FIGS. 3A and 3B, display signal output interface 510 is disposed on the top of housing 200A. In this exemplary embodiment it is assumed that the display signal will be delivered to the video display though this interface. The specific electrical connector configuration in output interface 510 is a design choice and will depend, at least in part, on what level of video signal processing is performed on-board surgical tool 10 and how much is off-loaded to a remote video processing unit. In some embodiments output interface 510 may be an analog interface such as S-video, for example, while in other embodiments it may conform to a digital video standard. In other embodiments, wherein the display signal is delivered to the video display wirelessly, the wireless version of display signal output interface 510 may be internal to housing 200A and would not therefore be visible in this view. In yet another variation, a wireless transmitter module may be connected to display signal output interface 510 to provide wired or wireless display communication capabilities with the same system embodiment.

The exemplary embodiment illustrated in these figures, it should be noted, is a baseline configuration in which certain features have been moved to remote modules. For example, the exemplary embodiment does not contain on on-board power supply, that is, a battery. In this embodiment power for the video camera and illumination subsystem is brought in, typically, through interface 510. In other embodiments a battery compartment for a thin battery is built into housing 200A, typically in reaction grip 212. A suitable battery for this embodiments is a lithium-ion battery available as Part NB-5L from Canon, U.S.A. Inc., One Cannon Plaza, Lake Success N.Y. 11042.

Figure 3C:
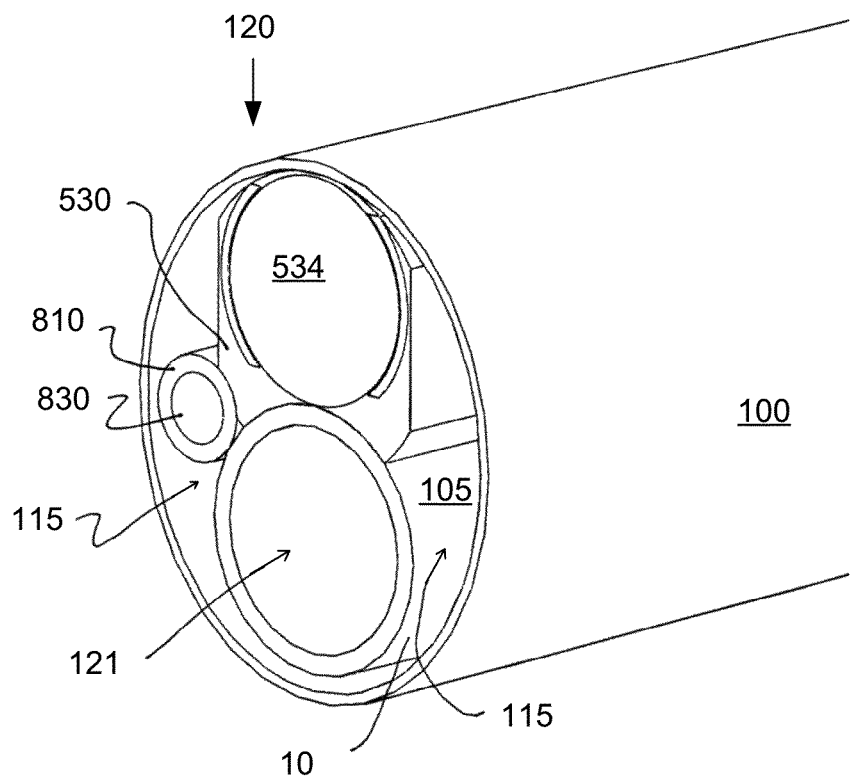
FIG. 3C is a detail illustration of the distal end of tubular body assembly according to an exemplary embodiment.

FIG. 3C is a detail illustration of the distal end of tubular body assembly 100. The open aperture distal end 121 of guide channel 105 is generally flush with the end of tubular body assembly 100 as is the irrigation port 820 of fluid transport tube 810. Video camera head 530 is also disposed at the distal end of body assembly 100. In this view, a lens 534 is disposed to look out toward the surgical field beyond distal end 120. Generally, lens 534 is preferably set back slightly from being flush with the end of tubular body assembly 100 for self-protection and cleanliness. Although not illustrated, the output tips of the optical fibers carrying illumination from a source in handle assembly 200 are disposed in otherwise vacant spaces 115 at distal end 120.

Figure 4C:
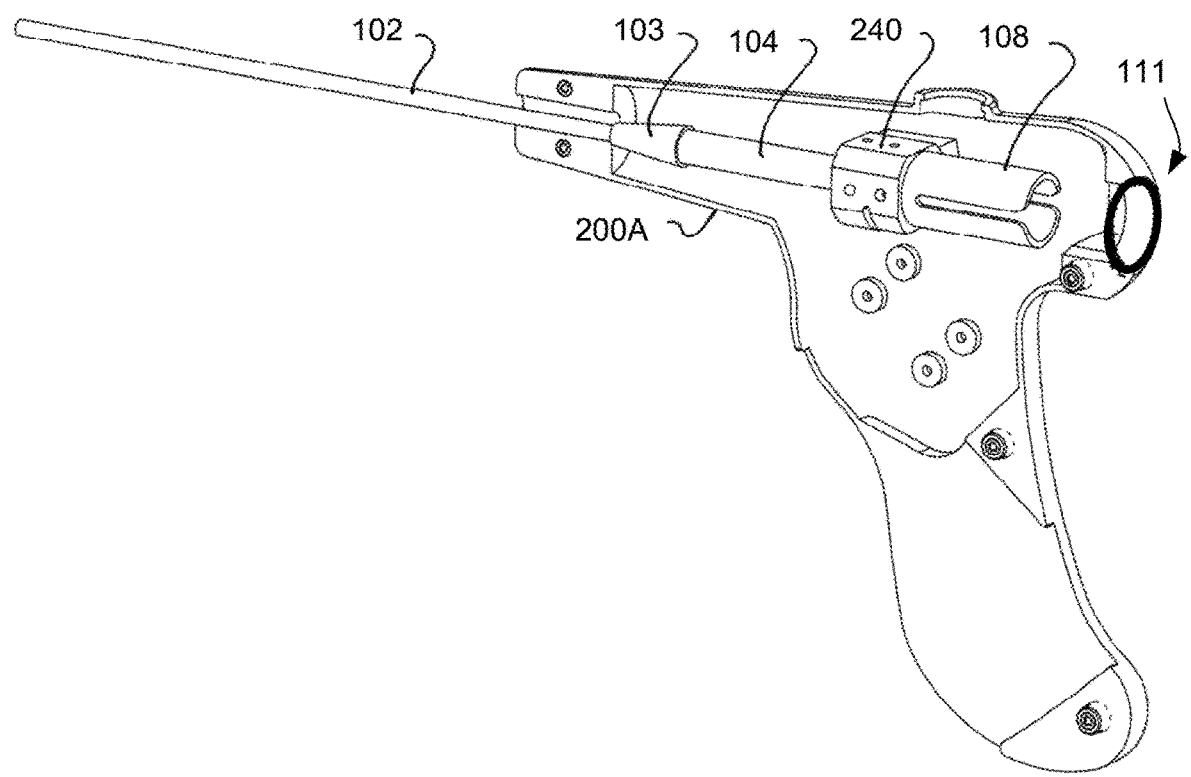
FIG. 4C is an isolated illustration of a guide channel according to an exemplary embodiment.

Turning to FIGS. 4A and 4B in general and to FIG. 4C in specific, guide channel 105, in this exemplary embodiment, is extended beyond the distal end of tubular body assembly 100 and is segmented, being formed from a series of sequentially smaller diameter segments that help funnel a normally open-jawed surgical instrument end effector from insertion through large aperture insertion port 111 to narrow aperture distal end 121. Sequentially, the elements forming guide channel 105 are: insertion port 111, a drive-pin guide 108, the lumen of axial retainer 240, a transfer tube 104, a transition cone 103, and a terminal tube 102. Of these elements, all but terminal tube 102 are disposed within housing 200A of control handle 200.

It will be noted that drive-pin guide 108, in addition to being part of the guide channel for the instrument effector subassembly, is also adapted to guide drive pins 1327 on axial force transfer collar 1320 to their proper position for engagement with force transfer yoke 227. More specifically, in this exemplary embodiment drive-pin guide 108 is substantially a thin walled cylinder with one or more drive-pin guide slots 107 disposed in the cylinder wall. Drive-pin guide slots 107 extend distally from the proximal rim of cylindrical drive-pin guide 108 to location that by design is aligned with the neutral position of yoke 227 and the drive-pin slots 229 therein. Typically there are two drive-pin guide slots 107 in drive-pin guide 108, the two slots being disposed diametrical opposed on drive-pin guide 108 and further typically being disposed in the X-Y plane indicated in the figure.

Transfer tube 104 and transition cone 103 are unexceptional. Transfer tube 104 is a cylindrical tube to guide the tip of a surgical instrument between the distal end of retainer block 242 and the proximal opening in transition cone 103.

In one exemplary embodiment surgical tool 20 is designed to accommodate 3 millimeter surgical instruments. In that embodiment, transfer tube is typically 5.6 millimeters in diameter. Transition cone 103 is a hollow, frustrated cone with a 5.6 millimeter base that is its proximal opening and a 3.4 millimeter aperture as it distal opening. Transition cone 103 guides the tip of a surgical instrument from the distal end of transfer tube 104 to proximal end of terminal tube 102. A conical shape is used for this transition to automatically close down any open elements of the surgical instrument's end effector to fit into terminal tube 102. Terminal tube 102 is the final, distal element of guide channel 105. Terminal tube 102 in one exemplary embodiment is 3.4 millimeters in diameter.

Figure 4D:
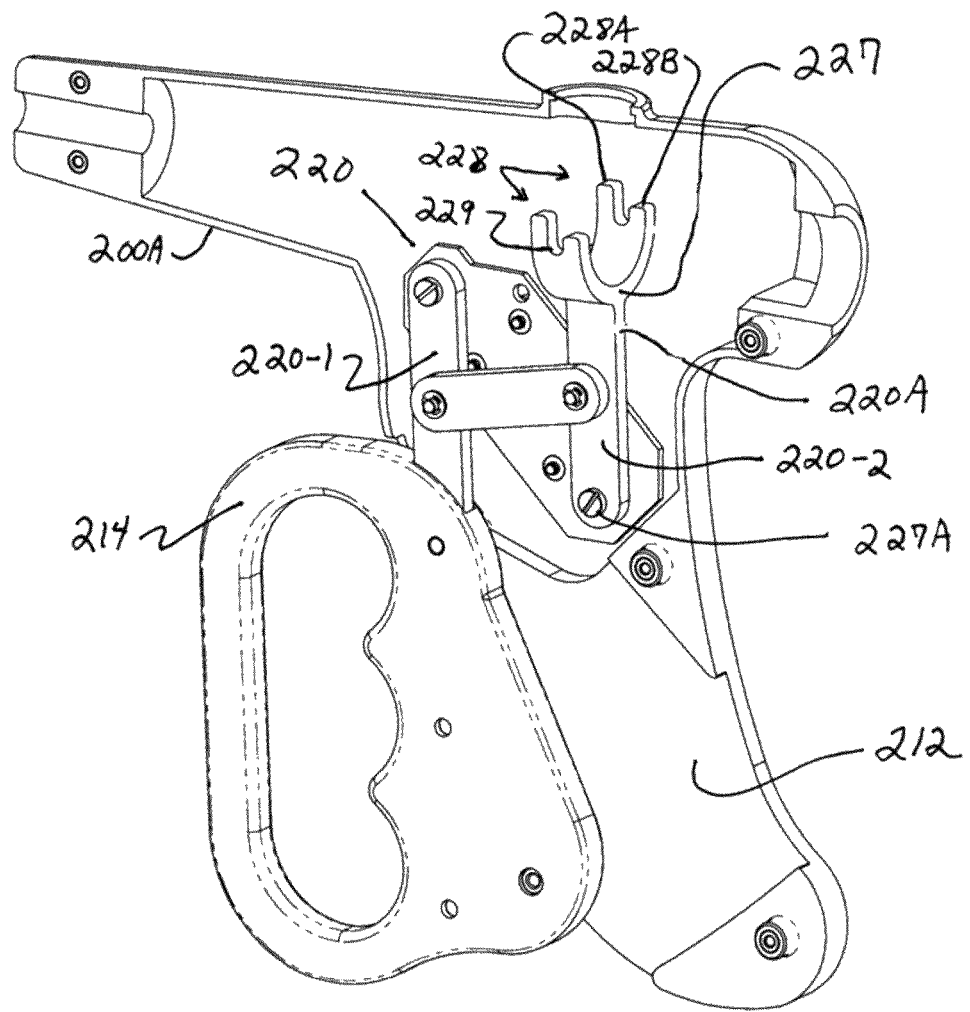
FIG. 4D is an isolated illustration of a force/motion transfer mechanism according to an exemplary embodiment.

Returning to control handle assembly 200, as illustrated in FIG. 4D, articulated grip 214 is attached to a first linkage element 220-1 in linkage set 220. Linkage set 220 converts the arcuate motion of linkage element 220-1 into a similar but inverted arcuate motion of a second linkage element 220-2. In this embodiment, linkage element 220-2 also comprises stalk 220A which carries force transfer yoke 227. Transfer yoke 227 is disposed at the opposite end of stalk 220A from a pivot point 227A and thus swings in an arc whose tangent is substantially parallel to the axis of guide channel 105. Thus, squeezing or compressing articulating grip 214 toward reaction grip 212 drives yoke 227 on a substantially rearward direction.

In this exemplary embodiment, force transfer yoke 227 comprises a head piece 228 having two prongs in which the two prongs are disposed at diametrically opposed locations across channel guide 105, generally towards proximal end 110. Each prong 228 has an open ended drive-pin slot 229, the slots being oriented substantially perpendicular to the axis of channel guide 105 when stalk 220A is in its nominal position, that is, substantially parallel to the Z-axis of the figure. In this exemplary embodiment drive-pin slot 229 divides the tip of prong 228 into two arms of different lengths: long arm 228A and short arm 228B. Long arm 228A is disposed to the distal side of drive-pin slot 229 whilst short arm 228B is disposed on the proximal side of drive-pin slot 229. As will be discussed below, the different lengths of long arm 228A and short arm 228B are designed to facilitate engagement and disengagement of drive pins 1327.

In other embodiments, guide channel 105 may comprise a single drive-pin guide slot 107 disposed, for example, along the bottom of guide channel 105. In such an embodiment transfer yoke 227 may comprise a single drive-pin slot at the top of stalk 220A designed to engage a single drive pin.

Figure 5A:
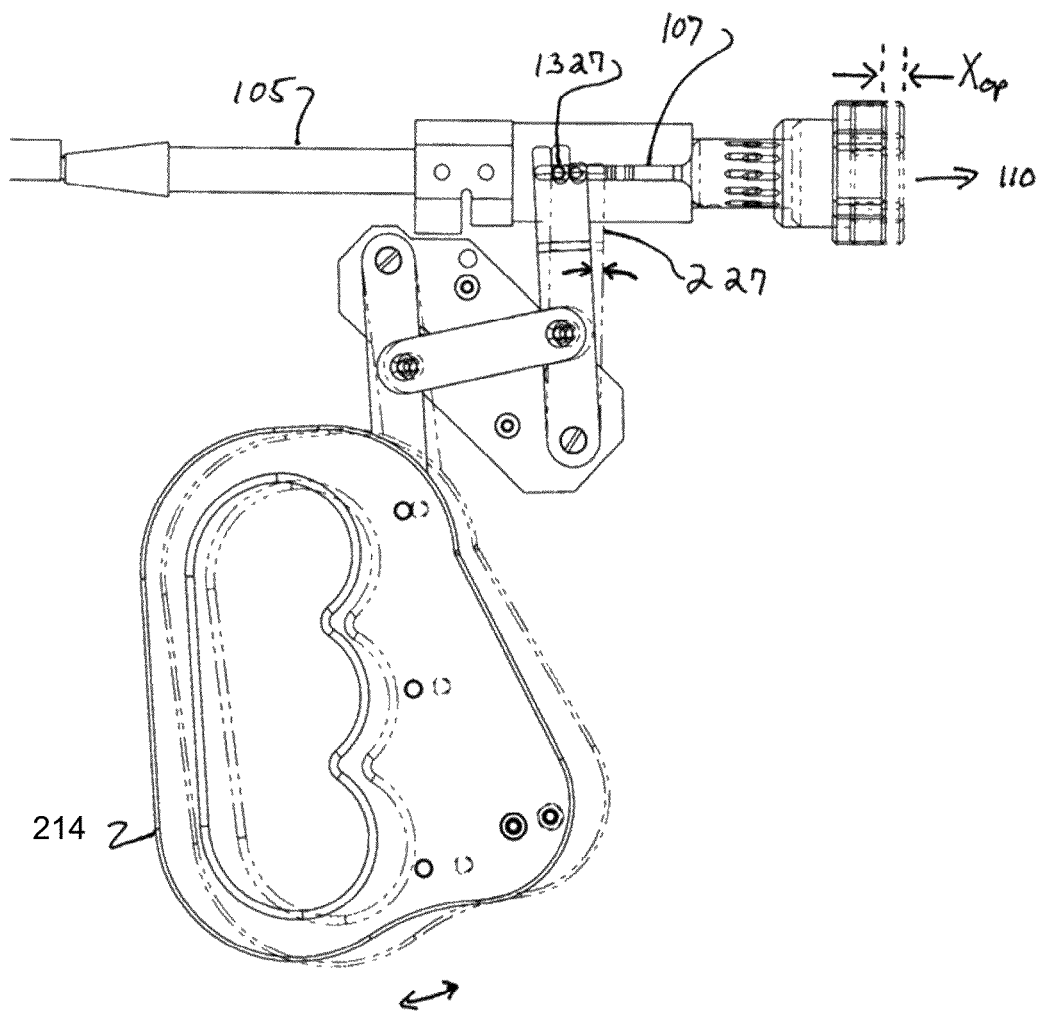
FIG. 5A is a detailed isolated illustration of a force transfer yoke showing its operational range according to an exemplary embodiment.

Transfer yoke 227 may be positioned over a continuous range of positions by the degree of compression of articulated grip 214 towards reaction grip 212. As illustrated in FIG. 5A with solid lines, the nominal "rest" position for transfer yoke 227, that is, its position when no compression is applied to articulated grip 214 is a forward operating position. As compression is applied to articulated grip 214, transfer yoke 227 moves toward proximal end 110, ending in the position illustrated in phantom (dashed lines) in FIG. 5A. It should be noted that this yoke motion, when a surgical instrument is installed in guide channel 105, will pull drive pins 1327 in the proximal direction to operate the end effector on the surgical instrument. When articulated grip 214 is fully or partially uncompressed, force transfer yoke 227 moves distally. Thus, this range of yoke motion comprises a continuum of surgical instrument operational positions indicated in the figure as distance XOp ("X operational").

Figure 5B:
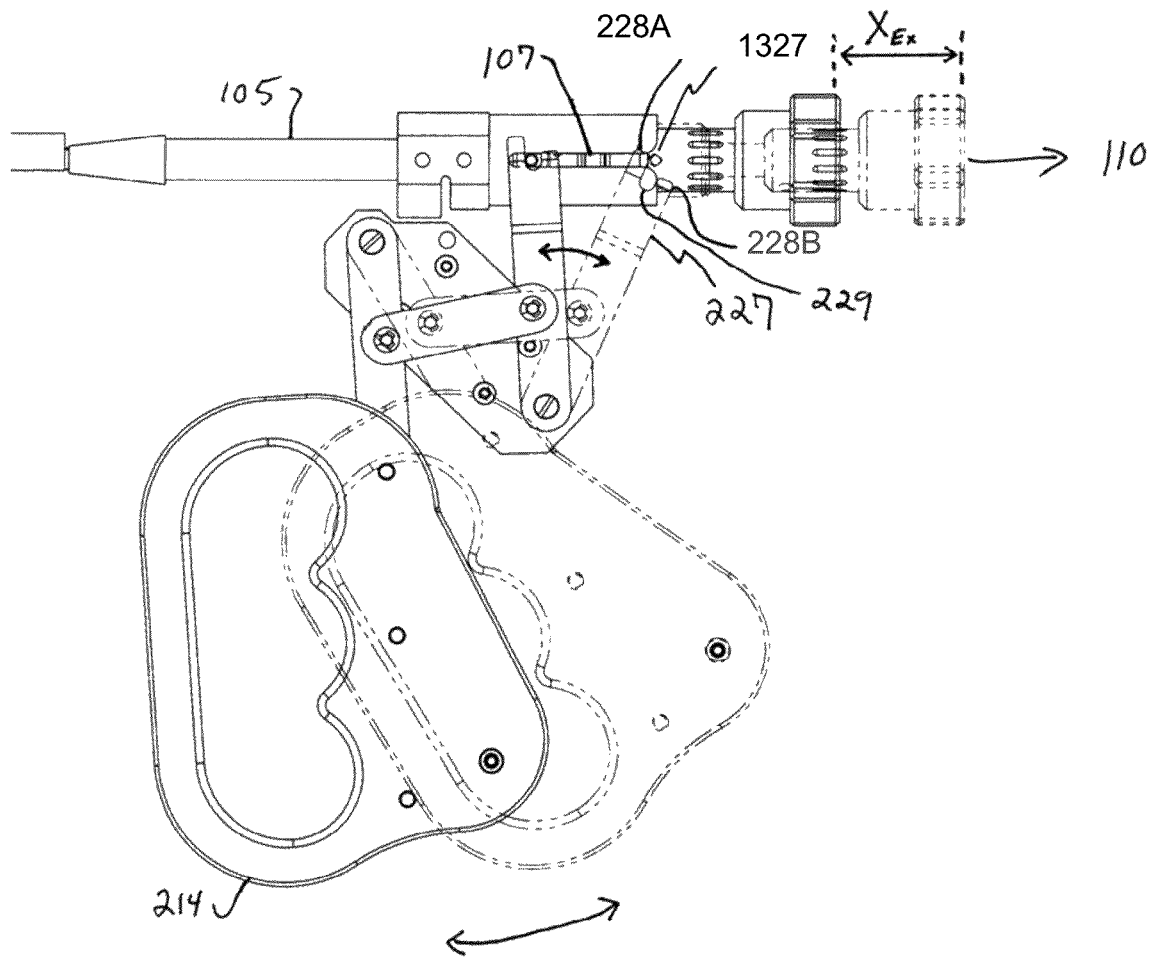
FIG. 5B is a detailed isolated illustration showing movement of a force transfer yoke to an instrument exchange position according to an exemplary embodiment.

Further compression of articulated grip 214 into reaction grip 212 moves yoke 227 even closer to proximal end 110. As shown in FIG. 5B, yoke 227 moves with an arcuate motion and therefore tilts as it translates toward proximal end 110 by a distance XEx ("X Exchange"). When articulated grip 214 is fully compressed, yoke 227 is disposed in its instrument exchange position, illustrated in phantom in the figure. In the instrument exchange position, the top edge of long arm 228A is still in contact with drive pin 1327, pushing it toward proximal end 110, while the top edge of short arm 228B has dropped below drive-pin guide slot 107, thereby allowing the surgical instrument attached to drive pin 1327 to be withdrawn proximally through insertion port 111 (not illustrated in FIG. 5B). Similarly, as will be obvious, a surgical instrument with drive pins 1327 may be inserted through insertion port 111 while yoke 227 is in the instrument exchange position. It will be noted that when a surgical instrument 50 is disposed in surgical tool 20, force transfer yoke 227 can be moved into the instrument exchange position only when the axial retainer is released.

Figure 4E:
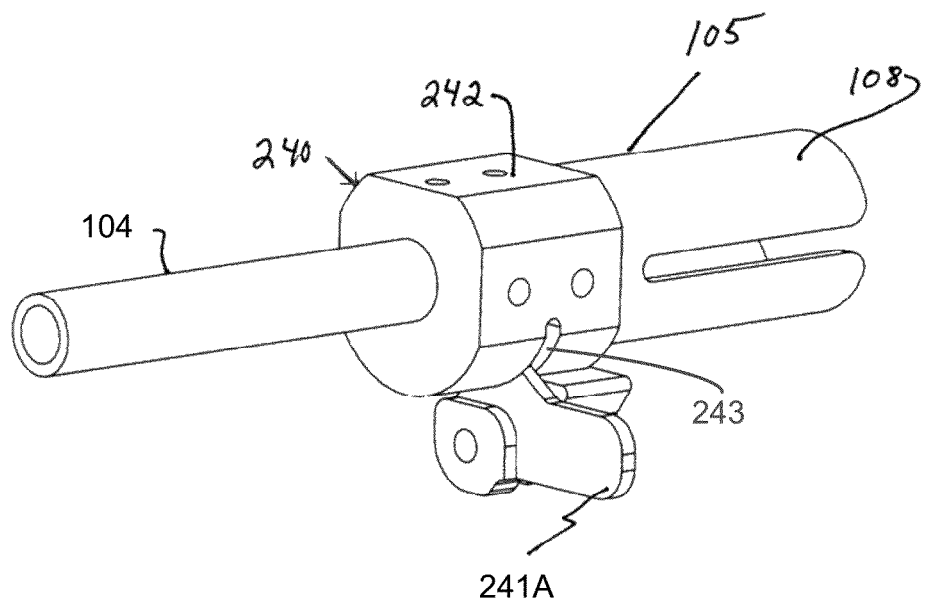
FIG. 4E is an isolated illustration of an axial retainer according to an exemplary embodiment.

Control handle assembly 200 further comprises axial retainer 240. As illustrated in FIG. 4E, axial retainer 240, in this exemplary embodiment, comprises a retainer block 242 and retaining bar 241. As has been described above, retainer block 242 comprises a lumen passing through it along the axis of control guide 105, the lumen functioning as part of the guide. Retaining bar 241 is, in this embodiment, L-shaped, with the vertical segment of the "L" being disposed in a slot 243 in retainer block 242 and the horizontal segment of the "L" disposed to protrude through housing 200A, as illustrated in FIG. 3A to allow a surgeon to adjust retaining bar 241 by pushing on tip 241A. In other embodiments, axial retainer 240 may be configured differently, for example, retainer 240 may comprise a dowel or peg that can be slid into and through retainer block 242 and into its lumen. The dowel or peg may enter the lumen directly pointing to the central axis, in which configuration it should stop short of interface connector 1305 or preferably it may enter the lumen above or below the central axis by a large enough distance to pass by interface connector 1305. When inserted, the dowel or peg performs the same function as retaining bar 241, namely to restrict the proximal motion of any installed surgical instrument.

Figure 4F:
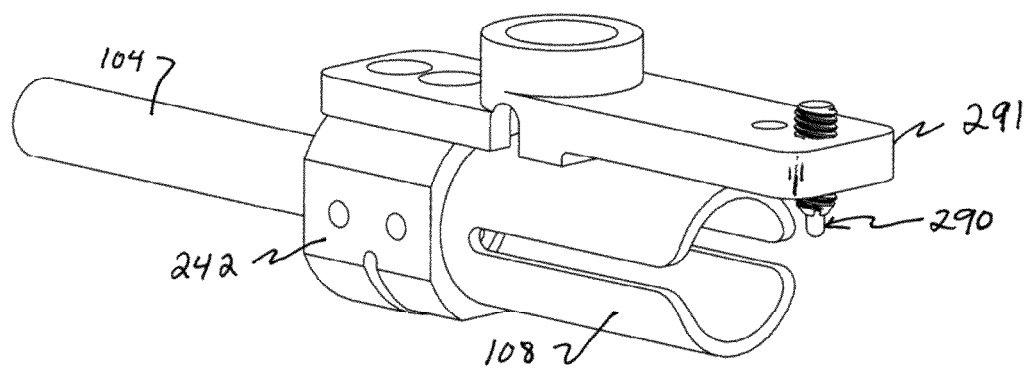
FIG. 4F is an isolated illustration of a rotation captivation mechanism according to an exemplary embodiment.

As illustrated in FIG. 4F, control handle assembly 200 also comprises rotation captivation mechanism 290. Captivation mechanism 290 is designed to engage with a co-operatively designed element on surgical instrument 50. In one exemplary embodiment, the co-operatively designed element on instrument 50 comprises a cylindrical rotation index collar 1390, around which a series of indented grooves are disposed. Therefore, in this embodiment, the captivation mechanism 290 is a spring-loaded ball plunger disposed in a mounting bracket 291 inside control handle assembly 200 and further disposed to project into the open lumen of channel guide 105. In the particular exemplary embodiment illustrated in the figures, captivation mechanism 290 is disposed near proximal end 110. When surgical instrument 50 is installed inside guide channel 105, the spring-loaded ball reaches rotation index collar 1390 and engages as a detent with one of the series of indented grooves therein. As is typical with a detent, surgical instrument may be rotated and "clicked into" any of the angular positions defined by the indented grooves. Surgical instrument is retained in the detent until intentionally rotated to another detent-defined angular orientation.

The exemplary embodiment of surgical tool 10 depicted in the FIGS. 3, 4, and 5 further comprises a video imaging subsystem and an illumination subsystem, only parts of which appear in the mechanical drawings above. FIG. 1 illustrates the general disposition of these subsystems in functional block diagram format. In the exemplary embodiment, the video imaging subsystem comprises video camera head 530 disposed at the distal end of tubular body 100, an interconnecting video signal wire bundle 524 disposed to connect camera head 530 to signal output interface 510, and signal output interface 510. In other, more completely self contained embodiments, video signal wire bundle 524 terminates at video processor 520 disposed in control handle assembly 200 and an output video signal wire bundle coveys the video image signals to signal output interface 510. In yet other embodiments, signal output interface conforms to a wireless, short-range communications protocol such as Bluetooth or Zigby, or to a wireless computer network using one of the protocols defined in IEEE 801.11. In a wireless environment, signal output interface 510 may be contained completely within exterior housing 200A, that is, signal output interface 510 would not be visible or accessible during normal operation. In yet other embodiments, the signals available at output interface 510 may be connected to a wireless communications module, also called a "dongle", wherein the video signals are transmitted to a remote receiving module, presumably connected to a video display device.

In this exemplary embodiment, as mentioned above, signals from camera head 530 are connected directly to signal output interface 510. In the exemplary embodiment, the power supplies, controls and video processor for the video imaging subsystem are disposed in an external, auxiliary unit. In other embodiments the video processor and/or power supply and/or video imaging subsystem controls are disposed internally to surgical tool 20.

Figure 6:
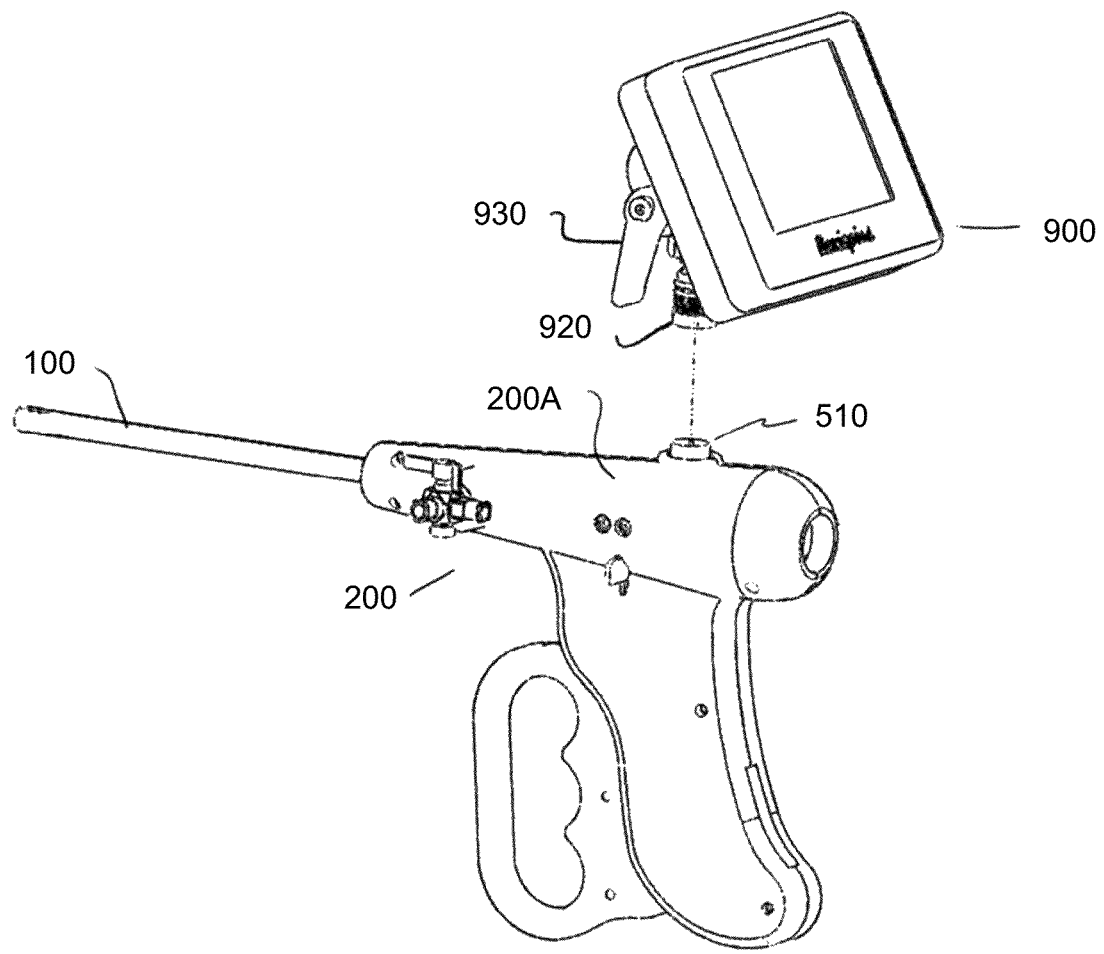
FIG. 6 is a partially exploded view of a surgical system illustrating a video display according to an exemplary embodiment.

In some embodiments, the above mentioned external, auxiliary unit comprises a video display. FIG. 6 illustrates a partially exploded view of a endoscopic surgical system 10 with an exemplary embodiment of an external, auxiliary unit comprising a video display 900. In one exemplary embodiment the video display comprises an LCD color monitor with 640×480 pixels on a 3.5" diagonal screen such as part # AND-TFT-35VX-KIT sold by Purdy Electronics Corporation, 720 Palomar Avenue, Sunnyvale, Calif. 94085. As will be understood by one of ordinary skill in the art of packaging electronics, video display 900 also comprises additional internal electronic components to convert the signals available on signal output interface 510 into appropriate drive signals for the LCD. Furthermore, as mentioned above, this particular exemplary embodiment of the surgical tool 20 does not have an internal power supply (e.g., battery) so power for surgical tool 20 must be supplied through interface 510. In the exemplary embodiment of FIG. 6 the battery is in video display 900. Finally, again as will be understood by one of ordinary skill in the art, video display 900 comprises several mechanical adaptations for use with surgical tool 20. For example, video display 900 comprises an electrical/mechanical connector 920 by which display 900 is attached to interface 510 and by which signals and power are interchanged between display 900 and tool 20. In some embodiments, display 900 includes display position-adjusting/locking mechanisms 930.

Returning to FIG. 3C, video camera head 530 is disposed at distal end 121 of tubular body 100. As is conventionally done, video camera head 530 comprises a commercially available video array sensor chip, not illustrated, which chip is normally available mounted on a miniature circuit board. The sensor chip-on-board is integrated with an imaging lens 534, the distal face of which is visible in FIG. 3. In this exemplary embodiment, the sensor chip is part # OV6930 manufactured by OmniVision of 4275 Burton Drive, Santa Clara, Calif. 94054, and the designers have selected a part # LP10120IR-M lens from Misumi Electronics Corp., 5F-3, No. 70, Jian 6th Rd., Zhonghe Dist., New Taipei City 235, Taiwan (R.O.C to provide an image field of about 70 degrees focused about 20 millimeters in front of (e.g., distal of) lens 534.

Returning to the functional block diagram in FIG. 1 and the exemplary embodiment of surgical tool 10 depicted in the FIGS. 3, 4, and 5, illumination subsystem 600, only parts of which appear in the latter figures, comprises light source assembly 620, fiber bundle 645, and electrical wiring to connect source assembly 620 to power supplies and control switches. Fiber optic illumination systems are well known by ones of ordinary skill in the art. In this exemplary embodiment, the designers have selected to use 50 micron optical glass fibers 640, formed into a bundle at proximal end by a 2 mm OD ferrule (not illustrated) and coupled to an LED light source house in assembly 620. In this exemplary embodiment, the LED receives its power and control via interface 510; that is, in this particular embodiment the designers have not included a power source 550 (e.g., a battery) in handle assembly 200. The exemplary embodiment comprises a 26 lumen, "white light" LED such as part # AT2117QR425ZS-VFS-W2 available from Kingbright Corporation, 225 Brea Canyon Rd, City of Industry, CA 91789.

Surgical system 10 also comprises one or more surgical instruments 50 designed to operate in conjunction with surgical tool 20. As illustrated in FIG. 7A, FIG. 7B and FIG. 7C, one exemplary surgical instrument 50 comprises instrument effector subassembly 1200 and handle engagement interface adaptor 1300. In the exemplary embodiment, instrument effector subassembly 1200 is a customized version of a model 31-4308 Sklartech 5000™ Miniature Grasping Forceps available from Sklar Instruments, 889 S. Matlack St. West Chester, Pa. 19382, wherein the only customization was to shorten the length of instrument, leaving the end effector and proximal interface unchanged. It should be noted that any of the Sklartech 5000 line of surgical instruments could be similarly customized. It should further be noted that the use of a commercially available instrument effector subassembly in general and the use of an effector subassembly from Sklar in particular was merely a design choice and is in no way limiting.

As illustrated in FIG. 7B and FIG. 7B1 in detail, the instrument effector subassembly 1200 extended sheathing body 1205, end effector 1210, a driving connector (not illustrated), axial retaining collar 1240, and a driving connector attachment 1260 is used as-supplied by the vendor, except for the aforementioned shortened length, and is familiar to one of ordinary skill in the art of endoscopic surgical instruments. Vendor supplied instrument effector subassembly 1200 comprises axial retaining collar 1240. Axial retaining collar 1240 is a substantially solid metal annulus that is rigidly attached to sheathing body 1205 to prevent any substantive axial or rotational relative displacement between the two. Distal face 1243 of axial retaining collar 1240 seats against a proximally facing structural surface inside axial retainer 1240 to prevent instrument 20 from moving further towards distal end 120 and proximal face 1242 of axial retaining collar 1240 provides the surface against which retaining bar 241 bears to lock instrument 50 in its proper location axially within guide channel 105.

Axial retaining collar 1240 and a driving connector attachment 1260 also comprise the instrument effector subassembly's interface between it and tool interface connector 1305. As illustrated in the detail illustration in FIG. 7B1, the driving connector in this exemplary embodiment is terminated at its proximal end with driving connector attachment 1260 in the form of a ball-tipped post. The post and ball tip are disposed in the center of axial retaining collar 1240 when free standing. Pulling attachment 1260 axially in the proximal direction relative to the retaining collar 1240 operates end effector 1210. Again note that this design is specific to the exemplary embodiment using Sklartech 5000 series instruments and that equivalent embodiments may be designed for instruments obtained from other sources or custom produced.

Returning to FIG. 7B, surgical instrument 50 further comprises handle engagement interface adaptor 1300. Interface adaptor 1300 comprises tool interface connector 1305 that is joined to instrument effector subassembly 1200 and which moves axially to operate end effector 1210 and moves rotationally to rotate end effector 1210 relative to sheathing body 1205. In this embodiment, tool interface connector 1305 is designed in coordination with axial retaining collar 1240 and driving connector attachment 1260 to transfer rotational torque and axial motion or force from the former to driving connector 1220.

Turning to FIG. 7C and detail FIG. 7C1, tool interface connector 1305 comprises a substantially solid rod having a proximal end 1306 and a distal end 1307. In this embodiment, distal end 1307 has been designed to fit into retaining collar 1240 and to capture and retain the ball-tipped post of driving connector attachment 1260. The capture and retention mechanism selected by the designer comprises an axial bore 1310 and three equally space radial cone-tipped set screws 1311.

Returning to FIG. 7B, the exemplary embodiment of handle engagement interface adaptor 1300 further comprises axial force transfer collar 1320, which transfers axial motion/force from force transfer yoke 227 to tool interface connector 1305. In one embodiment, axial force transfer collar 1320 comprises a toroidal ring 1325 from which one or more drive pins 1327 project radially. Drive pins 1327 have a diameter and projection length designed to allow them to extend through drive-pin guide slots 107 and further through drive-pin slots 229. Ring 1325 is disposed to encircle tool interface connector 1305. The interior diameter of the hole in ring 1325 is slightly larger than the exterior diameter of tool interface connector 1305 to allow ring 1325 to smoothly rotate about connector 1305. Ring 1325 is captivated axially by two retainers 1328 disposed at its proximal and distal ends. Thus, ring 1325 can spin in place axially on tool interface connector 1305.

In the exemplary embodiment, handle engagement interface adaptor 1300 also comprises rotation index collar 1390. Rotation index collar 1390 may be a ring or an end cap disposed on distal end 1307 of tool interface connector 1305. Index collar 1390 is typically rigidly attached to interface connector 1305 in both the axial and rotational degrees-of-freedom but must be attached to at least prevent a rotational motion about tool interface connector 1305. Index collar 1390 is designed to work co-operatively with rotation captivation mechanism 290 to position and hold surgical instrument 50 at one or more desired angular rotation positions relative to handle assembly 200. In the illustrated exemplary embodiment, rotation captivation mechanism 290 comprises a spring or ball plunger. Accordingly, in the exemplary embodiment index collar 1390 comprises a set of one or more shallow, axially-aligned, detent grooves 1395 disposed around the outer circumference of index collar 1390. Grooves are used instead of mere spherical indentations to accommodate the axial motion of interface connector 1305 when the surgical instrument is being operated.

Figure 8:
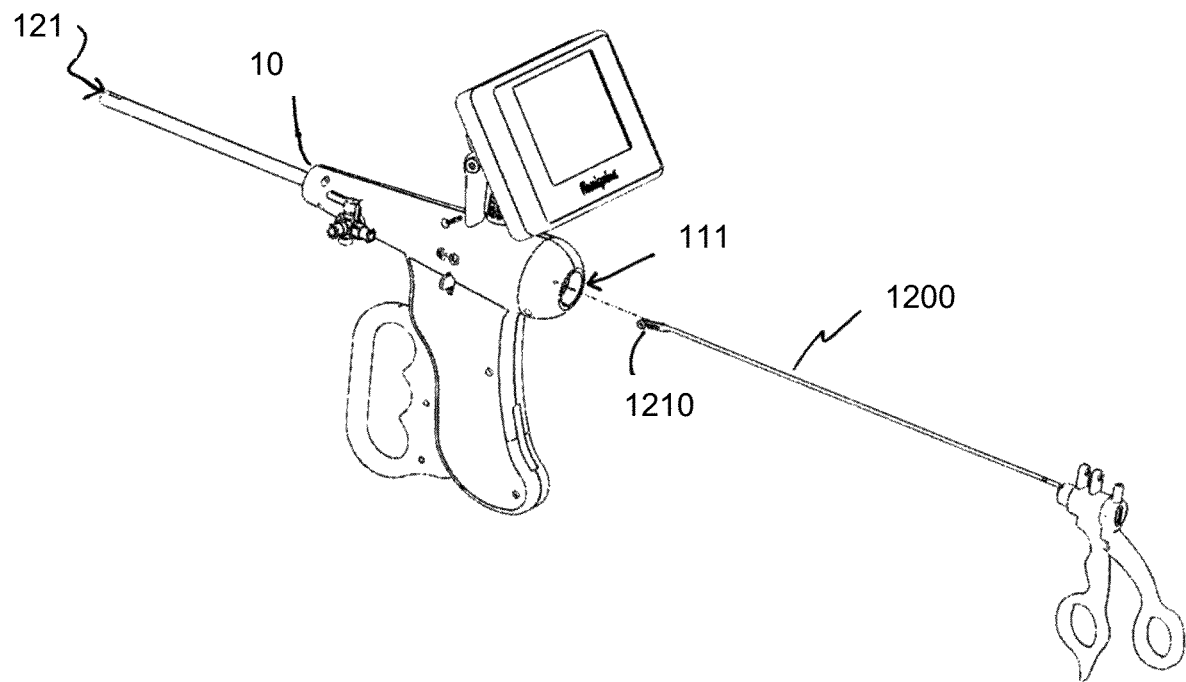
FIG. 8 illustrates an example of use of a commercially available, or industry standard, surgical instrument with a surgical tool according to an exemplary embodiment.

While embodiments of surgical system 10 comprise a number of inventive surgical instruments designed to perform a variety of surgical functions, the inventors recognize that there exist some specialized endoscopic surgical functions might not be available in the suite of surgical instruments 10, but that are available as commercially available, conventional instruments; for example, laser delivery fibers, shunt placement devices, and stent placement devices. Similarly, a surgeon may choose to use a prior art surgical instrument, as was shown in FIG. 2, forgoing the benefits of using an inventive surgical instrument 50. As illustrated in FIG. 8, inventive surgical tool 10 is backward compatible with prior conventionally designed surgical instruments. To use a conventionally designed instrument, a surgeon need only insert the conventional instrument's instrument effector subassembly 1200 into insertion port 111 and let guide channel 105 guide end effector 1210 to exit port 121. Guide channel 105 has been designed to an open lumen, allowing surgical tool 10 to function as just a video endoscope for conventional surgical instruments.

The present invention has been described herein in terms of several preferred embodiments. However, modifications and additions to these embodiments will become apparent to those of ordinary skill in the art upon a reading of the foregoing description. It is intended that all such modifications and additions comprise a part of the present invention to the extent that they fall within the scope of the several claims appended hereto.

What is claimed is:

1. A video endoscopic surgical tool comprising:
a substantially tubular body with one or more longitudinal channels, the tubular body has a proximal end and a distal end, where the proximal end is adapted to accept an endoscopic surgical instrument;
a handle assembly attached to the proximal end of the tubular body, the handle assembly comprising a reaction grip and an articulated grip, wherein the reaction grip is substantially rigidly connected to the tubular body, wherein the articulated grip is relatively-articulable with respect to the reaction grip and the tubular body, wherein the articulated grip is a control lever, and wherein said handle assembly is adapted to operate the endoscopic surgical instrument via articulating the articulated grip with respect to the reaction grip, when the endoscopic surgical instrument is present in the tubular body, wherein the handle assembly has a continuum of manually adjustable positions of the articulated grip with respect to the reaction grip, wherein the continuum of manually adjustable positions includes an endoscopic surgical instrument exchange position in which a yoke is configured to release the endoscopic surgical instrument, when present, and allow for removal of the endoscopic surgical instrument through the proximal end of the tubular body, wherein the yoke includes first and second arms and a drive pin slot defined between the first and second arms, wherein the second arm of the yoke drops below a drive pin guide slot to release a drive pin and allow withdrawal of the endoscopic surgical instrument through an insertion port at the proximal end of the substantially tubular body when the yoke is in the endoscopic surgical exchange position, wherein the continuum of manually adjustable positions includes a plurality of endoscopic surgical instrument operation positions whereby the yoke is configured to engage the drive pin between the first and second arms of the yoke so the handle assembly can operate the endoscopic surgical instrument, when present, by actuating the articulated grip with respect to the reaction grip throughout the plurality of endoscopic surgical instrument operation positions;
a video imaging subsystem built in whole or in part into the surgical tool, the subsystem comprising:
an image sensor positioned at a distal end of the surgical tool;
an image forming optical element optically coupled to the image sensor at the distal end of the surgical tool;
a video processor housed within the handle assembly; and
a video processor display signal output interface;
an illumination subsystem built in whole or in part into the surgical tool, the subsystem comprising:
one or more light sources housed within the handle assembly; and
a light transfer element extending from the one or more light sources to the distal end of the video endoscopic surgical tool; and
a power supply positioned in the handle assembly, the power supply configured to provide power to at least the video imaging subsystem and the one or more light sources.

2. The video endoscopic surgical tool of claim 1, further comprising:
the handle assembly further adapted to capture and to release the endoscopic surgical instrument.

3. The video endoscopic surgical tool of claim 2, further comprising a mechanical interface adapted for a detachable video display.

4. The video endoscopic surgical tool of claim 1, wherein the handle assembly further comprises control interface devices to control the video and illumination subsystems.

5. The video endoscopic surgical tool of claim 1, further comprising a video display mechanical interface.

6. The video endoscopic surgical tool of claim 1, further comprising a video display device adapted to receive video signals from the video processor via the video processor display signal output interface.

7. The video endoscopic surgical tool of claim 1, wherein a transition by the handle assembly from the endoscopic surgical instrument exchange position to a surgical tool operational position captures and engages an axial force transfer interface on the endoscopic surgical instrument in a co-operatively designed axial force transfer interface in the handle assembly.

8. The video endoscopic surgical tool of claim 1, further comprising an irrigation channel and a suction channel.

9. The video endoscopic surgical system of claim 1, wherein the first arm of the yoke is longer than the second arm of the yoke.

10. The video endoscopic surgical system of claim 1, wherein the yoke comprises first and second prongs, wherein the first prong comprises the first and second arms, and wherein the second prong comprises third and fourth arms.

11. The video endoscopic surgical system of claim 1, wherein the first arm is configured to engage the drive pin and the second arm is configured to be spaced away from the drive pin when the yoke is in the surgical instrument exchange position.

12. The video endoscopic surgical system of claim 1, wherein the yoke moves through an arcuate motion when moved between the surgical instrument exchange position and the endoscopic surgical instrument operation positions.

13. A video endoscopic surgical tool comprising:
- a substantially tubular body with one or more longitudinal channels, the tubular body has a proximal end and a distal end, where the proximal end is adapted to accept an endoscopic surgical instrument;
- a handle assembly attached to the proximal end of the tubular body, the handle assembly comprising at least two relatively-articulated elements, at least one of which is a control lever, wherein said handle assembly is adapted to operate the endoscopic surgical instrument via articulating the control lever, when the endoscopic surgical instrument is present;
- a video imaging subsystem built in whole or in part into the surgical tool; and
- an endoscopic surgical instrument axial captivation mechanism comprising a retaining bar that is operably connected to the handle assembly so as to move between a locked position in which the retaining bar is positioned in the longitudinal channel of the substantially tubular body to engage an axial retaining collar of the endoscopic surgical instrument and an unlocked position in which the retaining bar is positioned out of the longitudinal channel of the substantially tubular body, wherein the retaining bar is positioned in a first location that is out of the longitudinal channel and is configured to allow the endoscopic surgical instrument to pass into the tubular body when the retaining bar is in the unlocked position, wherein the retaining bar is positioned in a second location that is configured to engage the axial retaining collar of the endoscopic surgical instrument to retain the endoscopic surgical instrument in the tubular body when the retaining bar is in the locked position, wherein the endoscopic surgical instrument axial captivation mechanism is configured to axially captivate the endoscopic surgical instrument so as to constrain the endoscopic surgical instrument from moving axially within the longitudinal channel of the substantially tubular body.

14. The video endoscopic surgical tool of claim 1, further comprising an endoscopic surgical instrument rotational angle position retention mechanism adapted to interface with the endoscopic surgical instrument.

15. The video endoscopic surgical tool of claim 1, wherein the video endoscopic surgical tool is adapted to accept one or more conventional, or industry standard, endoscopic instruments.

16. The video endoscopic surgical tool of claim 15, further comprising the endoscopic surgical instrument, the endoscopic surgical instrument including at least one of a laser delivery fiber, a shunt placement device, a stent placement device, a suturing device, a surgical staple, a bipolar and monopolar cautery instrument, a curette, a guide wire, a balloon, and a flexible electronically controlled tooltip.

17. The video endoscopic surgical tool of claim 13, wherein the retaining bar is L-shaped and pivotally connected to the handle assembly.

* * * * *